United States Patent [19]

Kaneko et al.

[11] Patent Number: 5,349,066
[45] Date of Patent: Sep. 20, 1994

[54] BIFUNCTIONAL LINKING COMPOUNDS, CONJUGATES AND METHODS FOR THEIR PRODUCTION

[75] Inventors: Takushi Kaneko, Guilford; David Willner, Hamden; Ivo Monkovic, Durham; Robert S. Greenfield, Wallingford; Gary R. Braslawsky, Glastonbury, all of Conn.

[73] Assignee: Bristol-Myers Squibb Company, N.Y.

[21] Appl. No.: 865,062

[22] Filed: Apr. 8, 1992

Related U.S. Application Data

[62] Division of Ser. No. 522,996, May 14, 1990, Pat. No. 5,137,877.

[51] Int. Cl.$^5$ ............... C07D 211/72; C07C 229/00; C07C 241/00
[52] U.S. Cl. .................. 546/294; 546/300; 560/169; 564/18; 564/34; 564/149
[58] Field of Search ............... 546/294, 300; 564/34, 564/18, 149; 560/169

[56] References Cited

U.S. PATENT DOCUMENTS

| | | | |
|---|---|---|---|
| 4,112,217 | 9/1978 | Henry | 536/4 |
| 4,202,967 | 5/1980 | Tong et al. | 536/17 |
| 4,250,303 | 2/1981 | Wu et al. | 536/17 |
| 4,252,962 | 2/1981 | Rothgery | 564/18 |
| 4,282,031 | 8/1981 | Ratter et al. | 564/18 |
| 4,301,277 | 11/1981 | Acton et al. | 536/17 |
| 4,303,785 | 1/1981 | Umezawa et al. | 536/17 |
| 4,314,054 | 2/1982 | Acton | 536/17 |
| 4,464,529 | 8/1984 | Mosher et al. | 536/6.4 |
| 4,522,750 | 6/1985 | Ades et al. | 260/112 |
| 4,545,985 | 10/1985 | Pastan et al. | 424/85 |
| 4,590,001 | 5/1985 | Stjernholm | 530/394 |
| 4,591,637 | 5/1986 | Acton et al. | 536/6.4 |
| 4,647,655 | 3/1987 | Axen et al. | 546/294 |
| 4,675,382 | 6/1987 | Murphy | 530/350 |
| 4,970,303 | 11/1990 | Reardan et al. | 536/124 |
| 5,124,441 | 6/1992 | Carlsson et al. | 546/294 |

FOREIGN PATENT DOCUMENTS

| | | |
|---|---|---|
| 0294294 | 3/1988 | European Pat. Off. |
| 328147 | 8/1989 | European Pat. Off. |
| 274658 | 7/1986 | Japan |
| 57579 | 8/1986 | Japan |
| WO8800837 | 8/1987 | PCT Int'l Appl. |
| 2116979A | 2/1983 | United Kingdom |

OTHER PUBLICATIONS

Chemical Abstracts vol. 112, #98340f, 1989, Reardan et al, "Preparation of 5-pyridyl-alkyleneanilide, and related compounds a linking agent in preparation of coryugated antibodies".

Peterson et al., "Transport and Storage of Anthracyclines in Experimental Systems and Human Leukemia", *Anthracycline Antibiotics in Cancer Therapy,* Muggia et al., (Eds), p. 132 (Nijhoff Publ., 1982).

Wiernik, "Current Status of Adriamycin and Daunomy- (List continued on next page.)

*Primary Examiner*—C. Warren Ivy
*Assistant Examiner*—Raymond Covington
*Attorney, Agent, or Firm*—Merchant, Gould, Smith, Edell, Welter & Schmidt

[57] ABSTRACT

The present invention provides novel N-substituted hydrazine bifunctional compounds, novel N-substituted hydrazone derivatives of a cytotoxic reagent incorporating the bifunctional compounds, novel conjugates containing at least one cytotoxic reagent molecule reacted with the bifunctional compound and bound to a molecule reactive with a target cell population, methods for their production, and pharmaceutical compositions and methods for delivering cytotoxic reagents to a target population of cells. The hydrazone bonds of the conjugates of the invention permit the release of free cytotoxic reagent from the conjugates in the acidic external or internal environment of the target cells. The bifunctional compounds, derivatives, conjugates and methods of the invention are useful in antibody-or ligand-mediated drug delivery systems for the preferential killing of a target cell population to treat diseases such as cancers, infections and autoimmune disorders.

8 Claims, 9 Drawing Sheets

OTHER PUBLICATIONS cin in Cancer Treatment" in Anthracyclines: Current Status and new Developments, Crooke et al., (Eds.), pp. 273–294 (Academic Press 1980).

Hermentin and Seiler, "Investigations with Monoclonal Antibody Drug (Anthracycline) Conjugates", Behring Inst. Mitl. 82:197–215 (1988).

Gallego et al., "Preparation of Four Daunomucin-Monoclonal Antibody 791T/36 Conjugates with Anti–Tumour Activity" Int. J. Cancer 33:737–44 (2984).

Arnon et al., "In vitro and in vivo efficacy of conjugates of Daunomycin with Anti–Tumor Antibodies", Immunological Rev. 62:5–27 (1982).

Hurwitz et al., "The Covalent Binding of Daunomycin and Adriamycin to Antibodies, with Retention of both Drug and Antibody Activities", Cancer Res. 35:1175–1181 (1975).

Hurwitz et al., "The effect in vivo of chemotherapeutic drug–antibody conjugates in two murine experimental tumor systems", Int. J. Cancer 21:747–755 (1978).

Belles–isles et al., "In vitro activity of Daunomycin–anti-Alphafoetoprotein conjugate on mouse hepatoma cells", Br. J. Cancer 41: pp. 841–842 (1980).

Yamamoto et al., "Antitumor Activity of some Derivatives of Daunorubicin at the Amino and Methyl Ketone Functions" J. Med. Chem. 15:872–75 (1972).

Tong et al., "Antitumor Antrhacycline Antiboitics. Structure–Activity and Structure–Cardiotoxicity Relationships of Rubidazone Analogues" J. Med. Chem., 21(8):732–737 (1978).

Smith et al., "Adriamycin Analogues, 2, Synthesis of 13–Deoxyanthracyclines" J. Med. Chem., 21(3):280–283 (1978).

Brownlee, "Synthesis and Characterization of a Series of Bis–intercalating Bis–anthracyclines", J. Chem. Soc., pp. 659–661 (1986).

Hurwitz et al., "Soluble Macromolecules as Carriers for Daunorubicin" J. Appl. Biochem., 2:25–35 (1980).

Arnon and Hurwitz, "Monoclonal Antibodies as Carriers for Immunotargeting of Drugs", in Monoclonal Antibodies for Cancer Detection and Therapy, pp. 365–383 (1985), publ. Academic Press Inc. (London).

Hurwitz et al., "A Conjugate of Adriamycin and monoclonal antibodies to THY–1 antigen inhibits human neuroblastoma cells in vitro", Ann. N.Y. Acad. of Sci. vol. 417:125–136 (1983).

Dillman et al., "Preclinical Trials with Combinations and Conjugates of T101 Monoclonal Antibody and Doxorubicin", Cancer Res. 46:4886–4891 (1986).

Embleton, "Antibody Targeting of Anti-cancer Agents", in Monoclonal Antibodies for Cancer Detection and Therapy, Academ. Press, pp. 317–344 (1985).

Ford et al., "Localisation and toxicity study of a vindesine-anti-CEA conjugate in patients with advanced cancer", Br. J. Cancer, 47:35–42 (1983).

Cawley et al., "Epidermal Growth Factor–Toxin A Chain Conjugates: EGF–Ricin A is a Potent Toxin While EGF–Diptheria Frament A is Nontoxic", Cell 22:563–570 (1980).

Shimizu et al., "A Cytotoxic Epidermal Growth Factor Cross–Linked to Diptheria Toxin A–Fragment", FEBS Letters, 118(2):274–278 (1980).

Pastan and Fitzgerald, "New Cytotoxic Agents Created by the Fusion of Growth Factor and Modified Pseudomonas Exotoxin Genes", Proceed. Amer. Assoc. Cancer Res., 4th Ann. Conf. on Monoclonal Antibodies, 30:667 (1989).

Lorberbaum et al., "Cytotoxic activity of an interleukin 2–Pseudomonas exotoxin chimeric protein produced in Escherichia coli", Proc. Natl. Acad. Sci. USA, 85:1922–1926 (1988).

Chaudhary et al., "Activity of a recombinant fusion protein between transforming growth factor type and Pseudomonas toxin", Proc. Natl. Acad. Sci. USA, 84:4538–4542 (1987).

Siegall et al., "Cytotoxic activity of an interleukin 6–Pseudomonas exotoxin fusion protein on human myeloma cells", Proc. Natl. Acad. Sci. USA, 85:9738–9742 (1988).

Chaudhary et al., "Selective killing of HIV–infected cells by recombinant human CD4–Pseudomonas exotoxin hybrid protein", Nature:335:369–372 (1988).

Murphy et al., "Genetic construction, expression, and melanoma-selective cytotoxicity of a diptheria toxin–related–melanocyte–stimulating hormone fusion protein", Proc. Natl. Acad. Sci. USA, 83:8258–8262 (1986).

Varga et al., "Malanotropin–daunomycin conjugate shows receptor–mediated cytotoxicity in cultured murine melanoma cells", Nature, 267:56–58 (1977).

deDuve, "Lysosomes revisited", Eur. J. Bioch., 137:391–397 (1983).

Poznansky and Juliano, "Biological Approaches to the Controlled Delivery of Drugs: A Critical Review", (List continued on next page.)

OTHER PUBLICATIONS

*Pharm. Rev.*, 36:277–336 (1984).

Shen and Ryser, "Cis-aconityl spacer between daunomycin and macromolecular carriers: A model of PH-sensitive linkage releasing drug from a lysosomotropic conjugate", *Biochem. Biopys. Res. Comm.*, 102(3) 1048–1054 (1981).

Yang and Reisfeld, "Doxorubicin conjugated with a monoclonal antibody directed to a human melanoma-associated proteoglycan suppresses the growth of established tumor xenografts in nude mice", *Proc. Natl. Acad. Sci. USA*, 85:1189–1193 (1988).

Srinivasachar and Neville, "New protein cross-linking reagents that are cleaved by mild acid", Biochem., 28:2501–2509 (1989).

Hardy, "Purification and coupling of fluorescent proteins for use in flow cytometry", in *Immunochemistry*, vol. 1, Ed. Weir et al., Blackwell Sci. Publ., London (1967).

Casazza, "Experimental Studies on new Anthracyclines"in *Adriamycin: Its Expanding Role in Cancer Treatment*, Eds. Ogawa et al., Excerpts Medica, Publ., pp. 439–452 (1984).

DeWeger et al., "Eradication of Murine Lymphoma and Melanoma Cells by Chlorambucil-Antibody Complexes", *Immunol. Rev.*, 62:29–45 (1982).

Brown et al., "Structural Characterization of Human Melanoma-Associated Antigen p97 with monoclonal Antibodies", *J. Immunol.*, 127(2):539–46 (1981).

Pastan and Willingham, "The Pathway of Endocytosis", in *Endocytosis*, I:pp. 1–44 (1985).

Hellstrom et al., "Monoclonal Antibodies to Two Determinants of Melanoma-Antigen p97 Act Synergistically in Complement-Dependent Cytotoxicity", *J. Immunol.*, 127(1):157–160 (1981).

Zumach et al., "Chlorosulfenylated Carbonic Acid Derivatives", *Agnew Chem. Inter. Edit.*, 9:54–63 (1970).

Field et al., "Organic Disulfides and Related Substances, VIII. Preparation and Oxidation of Some Unsymmetrical Dialkyl and Alkyl Pyridinium Disulfides" *J. Organ. Chem.*, 29:1632 (1964).

Connor and Schroit, "Transbilayer Movement of Phosphatidylserine in Erythrocytes: Inhibition of Transport and Preferential Labeling of a 31 000-Dalton Protein by Sulfhydryl Reactive Reagents", *Biochem.*, 27:848–851 (1988).

Kim and Yi, "Di-2-Pyridyl Thionocarbonate. A new Reagent for the Preparation of Isothiocyanates and Carbodiimides", *Tetrahedron Letters*, 26(13):1661–1664 (1985).

Bruck et al., "One-Step Purification of Mouse Monoclonal Antibodies from Ascite Fluid by DEAE Affi-Gel Blue Chromatography", *J. Immunol. Meth.*, 53:313–319 (1982).

Ellman, "Tissue Sulfhydryl Groups", *Arch. Biochem. Biophys.*, 82:70–77 (1950).

Greenfield et al., "In Vitro Evaluation of Immunoconjugates Prepared by Linking Mitomycin C to Monoclonal Antibodies via Polyglutamic Acid Carriers", *Antibody, Immunoconjugates & Radiopharm.* 2:(3):201–216 (1989), Publ. M. Liebert.

WHERE R =

1. R=NNHCONH(CH$_2$)$_2$SSPy
2. R=NNHCONHNHCONH(CH$_2$)$_2$SSPy
3. R=NNHCSNHCH$_2$CH=CHCH$_2$SSPy
4. R=NNHCOO(CH$_2$)$_2$SSPy
5. R=NNH−Ar−CONH(CH$_2$)$_2$SSPy

Py = and Ar =

R = 1) CONH(CH$_2$)$_n$
   2) CONHNHCONH(CH$_2$)$_n$
   3) CSNH(CH$_2$)$_m$CH=CH—(CH$_2$)$_n$
   4) COO(CH$_2$)$_n$
   5) ArCONH(CH$_2$)$_n$

WHERE m,n ARE INTEGERS 1–10

R = 1) CONH(CH₂)ₙ
    2) CONHNHCONH(CH₂)ₙ
    3) CSNH(CH₂)ₘCH=CH-(CH₂)ₙ
    4) COO(CH₂)ₙ
    5) ArCONH(CH₂)ₙ

WHERE m,n ARE INTEGERS 1-10

R = 1) CONH(CH$_2$)$_n$
    2) CONHNHCONH(CH$_2$)$_n$
    3) CSNH(CH$_2$)$_m$CH=CH-(CH$_2$)$_n$
    4) COO(CH$_2$)$_n$
    5) ArCONH(CH$_2$)$_n$

WHERE m,n ARE INTEGERS 1-10

BIFUNCTIONAL LINKING COMPOUNDS, CONJUGATES AND METHODS FOR THEIR PRODUCTION

This is a division, of the application Ser. No. 07/522,996, filed May 14, 1990, now U.S. Pat. No. 5,137,877.

FIELD OF THE INVENTION

The present invention relates to novel bifunctional compounds, conjugates containing the compounds and methods for their production and use. More particularly, the invention relates to N-substituted hydrazine compounds that may be linked to molecules for targeting cell populations.

BACKGROUND OF THE INVENTION

Bifunctional compounds that permit the linkage of two or more molecules have been described. For example, bifunctional compounds for linking cytotoxic reagents to molecules for targeting cell populations are known. The bifunctional compounds must be capable of carrying and releasing these types of cytotoxic reagents in vivo, for example to provide sufficient, i.e. therapeutic, levels of the reagents in vivo, without damaging the activity of the targeting molecules. For certain applications, the formation of a conjugate containing a pH sensitive linkage between the reagent and targeting molecules of the conjugate providing release of the cytotoxic reagent in certain ranges of pH, is desirable.

Particularly useful reagents for treatment of cancers are the anthracyclines. Anthracyclines are antibiotic compounds that exhibit cytotoxic activity. Studies have indicated that anthracyclines may operate to kill cells by a number of different mechanisms including: 1) intercalation of the drug molecules into the DNA of a cell thereby inhibiting DNA-dependent nucleic acid synthesis; 2) production by the drug of free radicals which then react with cellular macromolecules to cause damage to the cells, or 3) interactions of the drug molecules with the cell membrane (Peterson et al., "Transport And Storage Of Anthracyclines In Experimental Systems And Human Leukemia", in *Anthracycline Antibiotics In Cancer Therapy*, Muggia et al. (Eds.), p. 132 (Martinus Nijhoff Publishers (1982); and Bachur, "Free Radical Damage", id. at pp. 97–102)). Because of their cytotoxic potential, anthracyclines have been used in the treatment of numerous cancers such as leukemia, breast carcinoma, lung carcinoma, ovarian adenocarcinoma, and sarcomas (Wiernik, "Current Status Of Adriamycin And Daunomycin In Cancer Treatment", in *Anthracyclines: Current Status And New Developments*, Crooke et al. (Eds.), pp. 273–94 (Academic Press 1980)). Commonly used anthracyclines include adriamycin (ADM also known as doxorubicin) and daunomycin (DAU also known as daunorubicin).

Although these compounds may be useful in the treatment of neoplasms and other disease states wherein a target cell population is sought to be reduced or eliminated, their therapeutic efficacy is often limited by the dose-dependent toxicity associated with their administration. For example, in the treatment of tumors, typical adverse side effects of these compounds include myelosuppression and cardiotoxicity (Crooke, "Goals For Anthracycline Analog Development At Bristol Laboratories", *Anthracyclines: Current Status And New Developments*, Supra, at p. 11). Attempts have therefore been made in the treatment of tumors to improve the therapeutic effects of these compounds by linking the anthracycline to antibodies directed against tumor-associated antigens to form immunoconjugates for selective delivery of the drugs to tumor cells. (Hermentin and Seiler, "Investigations with monoclonal antibody drug (anthracycline) conjugates", *Behring Insti. Mitl.* 82:197-215 (1988)). In this way, the drug can be delivered or "targeted" to the tumor site and its toxic side effects on normal cells in the body may be diminished. Immunoconjugates comprised of the anthracyclines ADM or DAU linked to polyclonal or monoclonal antibodies to tumor-associated antigens are known in the art (e.g. Gallego et al., "Preparation Of Four Daunomucin-Monoclonal Antibody 791T/36 Conjugates With Anti-Tumor Activity", *Int. J. Cancer* 33:737-44 (1984); and Arnon et al., "In Vitro And In Vitro Efficacy Of Conjugates Of Daunomycin With Anti-Tumor Antibodies", *Immunological Rev.* 62:5-27 (1982)).

The most frequently used approaches for the attachment of an anthracycline to an antibody have utilized a linkage at the amino sugar moiety of the anthracycline. For example, the amino sugar has been oxidized by sodium periodate treatment and directly attached to lysine residues on the antibody via Schiff base formation (Hurwitz et al., "The Covalent Binding Of Daunomycin And Adriamycin To Antibodies, With Retention of Both Drug And Antibody Activities", *Cancer Res.* 35:1175–1181 (1975)). Alternatively, anthracyclines have been linked to antibodies through carbodiimide-mediated linkage of the amino group of the anthracycline to carboxyl groups on the antibody (Hurwitz et al., supra) or an aminoalkyl group (Hurwitz et al., "The Effect in vivo of Chemotherapeutic drug-antibody conjugates in two murine experimental tumor systems" *Int. J. Cancer* 21:747-755 (1978)). These linkages are not easily hydrolyzed and make it difficult to control the release of the anthracycline. Anthracyclines have also been linked to antibodies by cross-linking the amino sugar of the drug and amino groups on the antibody with glutaraldehyde (Belles-Isles et al., "In Vitro Activity of Daunomycin-Anti-AlphaFetoprotein Conjugate On Mouse Hepatoma Cells", *Br. J. Cancer* 41, pp. 841–42 (1980)). However, studies with immunoconjugates in which the amino sugar portion of the anthracycline molecule was modified by linkage to the antibody indicate a loss of cytotoxic activity of the conjugated drug (Arnon et al., supra, at pp. 7-8). In addition, studies of anthracycline analogs indicate that modifications of anthracyclines at their amino sugars result in a decrease in the cytotoxic activity of the drug analog relative to the parent drug (Yamamoto et al., "Antitumor Activity of Some Derivatives of Daunomycin At The Amino And Methyl Ketone Functions", *J. Med. Chem.* 15:872-75 (1972)).

Still other immunoconjugates have been prepared wherein the anthracycline DAU has been linked directly to an antibody at the carbon-14 (C-14) position of the drug. However, the selective cytotoxic activity of these immunoconjugates toward tumor cells was not easily reproducible and was revealed consistently only at a concentration of 20 μg/ml (Gallego et al., supra).

Japanese patent application 274658 discloses the conjugation of an anthracycline to an antibody via a C-13 acylhydrazone linkage. This conjugation was accomplished using methods that involve derivatization of the antibody and subsequent reaction of that derivative with anthracycline. These methods are not favored because derivatization of the antibody involves undesirable non-specific reactions and yields very low anthracycline:antibody ratios. According to the first method, the antibody was treated with carbodiimide in the presence of hydrazine to yield a hydrazide antibody derivative which was then reacted with the anthracycline such that the anthracycline was linked directly to the antibody structure. The resulting immunoconjugates, however, are prone to aggregation of the antibody molecules. Furthermore, because this method requires carboxylic groups which may be limited in number, these immunoconjugates have low anthracycline:antibody ratios (approximately 1.1-1.3). The second method involves reacting the antibody with succinic anhydride to yield a hemi-succinate derivative of the antibody. This derivative was next reacted with hydrazine to yield an antibody hydrazide derivative which was then reacted with the anthracycline, daunomycin. This second approach is flawed in that the reaction of the antibody derivative with hydrazine is non-specific, leading to the production of a mixture of different antibody derivatives in addition to the desired hydrazide derivative. Thus, as indicated in the 274658 application, the molar ratio of anthracycline to antibody was very low (approximately 1, see Japanese application, page 264, column 1). See also, European patent application, Publication No. 294294, which discloses the conjugation of a C-13 hydrazone derivative of an anthracycline to the carbohydrate moiety of an antibody.

Other anthracycline hydrazones are disclosed in Tong et al., *J. Med. Chem.*, 21:732-37 (1978); Smith et al., *J. Med. Chem.*, 21:280-83 (1978); and Brownlee et al., *J. Chem. Soc.*, pp. 659-61 (1986). See also U.S. Pat. No. 4,112,217, which discloses bis-hydrazones of DAU and ADM.

In other studies, anthracyclines have been linked to high molecular weight carriers, such as dextran or polyglutamic acid, in order to potentiate the cytotoxic activity and reduce the toxicity of the drug (Arnon et al., supra, at p. 5 and Hurwitz et al., "Soluble Macromolecules As Carriers For Daunorubicin", *J. Appl. Biochem.* 2, pp. 25-35 (1980)). These carrier-linked anthracyclines have also been covalently bound to antibodies directed against tumor-associated antigens to form immunoconjugates for targeting of the cytotoxic drug specifically to tumor cells. For example, ADM has been linked to such an "anti-tumor" antibody via a carboxy-methyl-dextran hydrazide bridge wherein the ADM molecule was linked to a hydrazine derivative of carboxymethyl dextran at the C-13 carbonyl of the ADM to form a hydrazone. The antibody was then linked to the dextran hydrazide derivative with glutaraldehyde to form an adriamycin-dex-antibody conjugate (Arnon et al., "Monoclonal Antibodies As Carriers For Immunotargeting Of Drugs" in *Monoclonal Antibodies For Cancer Detection And Therapy*, Baldwin et al. (Eds.), pp. 365-83 (1985) and Hurwitz et al., "A Conjugate Of Adriamycin And Monoclonal Antibodies To Thy-1 Antigen Inhibits A Human Neuroblastoma Cells In Vitro", *Ann. N.Y. Acad. Sci.* 417, pp. 125-36 (1983)).

However, the use of carriers entails certain disadvantages. For example, carrier-containing immunoconjugates are quite large in size and are removed rapidly by the reticuloendothelial system in vivo (Dillman et al., "Preclinical Trials With Combinations And Conjugates Of T101 Monoclonal Antibody And Doxorubicin", *Cancer Res.* 46:4886-91 (1986)). This rapid removal of the carrier-containing immunoconjugates may not be advantageous for therapy because the conjugated drug may never reach its intended site of action, i.e., the target group of cells to be killed. In addition, the presence of the high molecular weight carrier may negatively affect the stability of the immunoconjugate and has been shown to reduce the binding activity of the antibody of the conjugate (Embleton et al., "Antibody Targeting Of Anti-Cancer Agents", in *Monoclonal Antibodies For Cancer Detection And Therapy*, Baldwin et al. (Eds.), pp. 323-24 (1985)). Furthermore, in studies with tumor cells, there is no evidence that high molecular weight carrier-containing immunoconjugates are able to localize to the tumor cells in vivo. (Compare Ford et al., "Localization And Toxicity Study Of A Vindesine-Anti-CEA Conjugate In Patients With Advanced Cancer", *Br. J. Cancer* 47:35-42 (1983), which demonstrates localization of directly-conjugated drug-antibody conjugates to tumor cells in vivo).

Thus, the conjugation of anthracyclines to antibodies by the use of specific linkages and carriers has been disclosed. As outlined above, the use of these immunoconjugates entails distinct disadvantages depending upon the specific linkage or carrier used.

Certain ligand-toxin conjugates have also been disclosed. U.S. Pat. No. 4,545,985, issued to Pastan, discloses an exotoxin conjugate wherein Pseudomonas exotoxin (PE) is linked to EGF in a ratio of 1:2 for use against cells having large numbers of EGF receptors. EGF-ricin A and EGF-diphtheria toxin conjugates have also been made; Cawley et al., "Epidermal Growth Factor-Toxin A Chain Conjugates:" EGF-Ricin A Is A Potent Toxin While EGF-Diphtheria Fragment A Is Nontoxic", *Cell* 22:563-70 (1980) and Shimizu et al., "A Cytotoxic Epidermal Growth Factor Cross-Linked To Diphtheria Toxin A-Fragment", *FEBS Letters* 118 (No.2):274-78 (1980)). Furthermore, Pseudomonas exotoxin fusion proteins have been prepared using proteins, polypeptides and growth factors such as TGF-α, IL-2, IL-6 and CD4 (Pastan et al., "Novel Cytotoxic Agents Created By The Fusion Of Growth Factor And Toxin Genes", *Fourth Internatl. Conference On Monoclonal Antibody Immunoconjugates For Cancer*, p. 36 (Mar. 30-Apr. 1, 1989); Lorberboum et al., *Proc. Natl. Acad. Sci. USA*, 85:1922-26 (1988); Chaudhary et al., *Proc. Natl. Acad. Sci. USA*, 84:4538-42 (1987); Siegall et al., *Proc. Natl. Acad. Sci. USA*, 85:9738-42 (1988); and Chaudhary et al., *Nature*, 335:369-72 (1988)). A diphtheria toxin-α-melanocyte stimulating hormone fusion protein has been made (Murphy et al., "Genetic Construction, Expression And Melanoma-Selective Cytotoxicity Of A Diphtheria Toxin-Related α-Melanocyte-Stimulating Hormone Fusion Protein", *Proc. Natl. Acad. Sci. USA*, 83:8258-62 (1986), and U.S. Pat. No. 4,675,382, issued to Murphy). Ligand conjugates comprising protein toxins, however, may prove to be immunogenic in xenogeneic hosts.

In addition, anthracyclines such as ADM or DAU have been chemically linked to certain protein or polypeptide ligands such as transferrin (United Kingdom patent application, GB 2116979 A) and melanotropin (Varga et al., "Melanotropin-Daunomycin Conjugate Shows Receptor-Mediated Cytotoxicity For Cultured Murine Melanoma Cells", *Nature* 267: 56-58 (1977)). PCT patent application WO 88/00837 describes EGF linked via a polymeric carrier to a cytotoxic substance such as DAU and U.S. Pat. Nos. 4,522,750 and 4,590,001 describe transferrin linked to vinca alkaloid and platinum, respectively.

The cytotoxic drug to be used in the immunoconjugate should be released via a conditional release mechanism, i.e. the cytotoxic drug should be released at a specific site rather than by a gradual, nonspecific site hydrolysis. It has been proposed that particular immunoconjugates are translocated to lysosomes (deDuve, "Lysosomes Revisited", *Eur. J. Biochem.* 137:391-397 (1983)), which are slightly acidic (pH 5.0 to 5.5) (Poznansky and Juliano, "Biological Approaches to the Controlled Delivery of Drugs: A Critical Review", *Pharmacol. Rev.* 36:277-336 (1984)). The use of acidic conditions to release conjugated drug has been reported in the development of cis-aconityl linkers to ADM (Shen and Reiser, "Cis-Aconityl Spacer Between Daunomycin and Macromolecular Carriers: A Model of pH-sensitive Linkage Releasing Drug From a Lysosomotrophic Conjugate", *Biochem. Biophys. Res. Commun.* 102:1048-1054 (1981) and Yang and Reisfeld, "Doxorubicin Conjugates With a Monoclonal Antibody Directed to a Human Melanoma-Associated Proteoglycan Suppresses the Growth of Established Tumor Xenografts in Nude Mice", *Proc. Natl. Acad. Sci.* 85:1189-1193 (1988)), and ketal linkers to diphtheria toxin (Srinivasachar and Neville, "New Protein Cross-Linking Reagents That Are Cleaved by Mild Acid", *Biochemistry* 28:2501-2509 (1989 )).

Greenfield et al. have recently described the formation of acid-sensitive immunoconjugates containing the acylhydrazine compound, 3-(2-pyridyldithio)proprionyl hydrazide conjugated via an acylhydrazone bond to the 13-keto position of the anthracycline molecule, and conjugation of this anthracycline derivative to an antibody or ligand molecule (Greenfield et al., European Patent Application No. 328,147, published Aug. 16, 1989).

It would be useful to provide additional bifunctional compounds that are structured to provide acid-sensitive linkage between molecules, including targeting and reagent molecules for use in therapy in vivo.

SUMMARY OF THE INVENTION

The present invention provides novel bifunctional compounds that are readily conjugated with useful molecules, and methods for preparing the bifunctional compounds. The bifunctional compounds contain a reactive pyridinyldithio or ortho-nitrophenyldithio group. The invention also provides novel conjugates containing cytotoxic molecules linked to the bifunctional compounds to form derivatives of the cytotoxic molecules and further conjugates containing the cytotoxic derivatives linked to a molecule capable of reacting with a target cell population to be killed. This targeting molecule can be a protein such as an antibody or a ligand such as bombesin or EGF.

According to one embodiment, a novel bifunctional compound, N-[2-[(2-pyridinyl)dithio]ethyl]hydrazinecarboxamide (compound 10) is synthesized and is used to form a semicarbazone derivative of ADM containing a semicarbazone bond at the C-13 position of the ADM that serves as the site of attachment of the ADM to compound 10.

According to another preferred embodiment, a novel bifunctional compound, 2-[[[2-[(2-pyridinyl)dithio]ethyl]amino]carbonyl]carbonic dihydrazide (compound 11a) is synthesized and is used to form a carbazone derivative of ADM containing a carbazone bond at the C-13 position of the ADM that serves as the site of attachment of the ADM to compound 11a.

In another preferred embodiment, a novel bifunctional compound, N-[4-[(2-pyridinyl)dithio]-2-butenyl]-hydrazinecarbothioamide (compound 12) is synthesized and is used to form a thiosemicarbazone derivative of ADM containing a thiosemicarbazone bond at the C-13 position of the ADM that serves as the site of attachment of the ADM to compound 12.

According to another preferred embodiment, a novel bifunctional compound, 2[(2-pyridinyl)dithio]ethyl hydrazinecarboxylate (compound 13) is synthesized and is used to form a hydrazone derivative of ADM containing a carboxylatehydrazone bond at the C-13 position of the ADM that serves as the site of attachment of the ADM to compound 13.

In yet another preferred embodiment a novel bifunctional compound, N-[2-[(2-pyridinyl)dithio]ethyl]-hydrazinobenzamide (compound 15), is synthesized and is used to form an arylhydrazone derivative of ADM containing an arylhydrazone bond at the C-13 position of the ADM that serves as the site of attachment of the ADM to compound 15.

According to still another embodiment of this invention, a number of molecules of the above novel anthracycline derivatives are linked to a molecule reactive with a selected target cell population. Preferably, the cell-reactive-molecule is an antibody, and is a monoclonal antibody. Each anthracycline derivative molecule is linked to the antibody via the bifunctional compound bound to the anthracycline via a semicarbazone, carbazone, thiosemicarbazone, carboxylatehydrazone or arylhydrazone bond at the C-13 position of the anthracycline molecule to form the novel immunoconjugates of the invention. For example, a preferred embodiment of the invention involves the synthesis of a novel adriamycin derivative molecule that is condensed with a thiolated antibody resulting in the attachment of the anthracycline to the antibody via the bifunctional compound. The hydrazone bond formed at the C-13 position of the ADM serves as the site of attachment to the ADM. In this embodiment a disulfide bond is present within the bifunctional compound through which it is attached to the antibody. According to another preferred embodiment, the adriamycin derivative molecule (ADM bound to the bifunctional compound) is reduced to generate a sulfhydryl group and the resulting derivative is condensed with a maleimide-derivatized antibody. This leads to the formation of an immunoconjugate having a N-substituted hydrazone bond as the site of the bifunctional compound attachment to the C-13 position of ADM and a thioether bond within the bifunctional compound through which it is attached to the antibody.

According to yet another preferred embodiment of the invention, the novel anthracycline derivatives may be covalently linked to ligands, such as bombesin, transferrin or EGF, resulting in the attachment of the anthracycline to the ligand via a bifunctional compound. As in the other embodiments described above, the anthracycline is attached to the bifunctional compound via a hydrazone bond formed at the C-13 position of the anthracycline. The ligand is preferably thiolated prior to linkage to the anthracycline derivative, but it may also be directly attached to ligands having an endogenous free thiol group.

As is evident from these embodiments, the present invention provides novel bifunctional compounds and derivatives of anthracyclines useful in the preparation of the conjugates of this invention.

The immunoconjugates of the present invention have an anthracycline: antibody molar ratio of at least 1:1 and up to 10:1, and preferably of approximately 4:1 to 10:1, and retain both antibody and cytotoxic drug activity for the killing of selected target cells. The anthracycline-ligand conjugates described herein preferably have an anthracycline:ligand ratio of at least 1:1 and up to 10:1, and preferably of-approximately 4:1 to 10:1. The acid-sensitive bond that is present at the site of attachment of the anthracycline to the bifunctional compound of these conjugates is ideally suited for the release of active drug under acidic conditions such as those typically encountered within a cell, e.g., in lysosomal vesicles.

The release of adriamycin by hydrolysis of each of the above named derivatives, as a function of pH, demonstrated that the new derivatives had wide ranging release rates under acidic conditions mimicking the lysosomal environment. These derivatives also demonstrated cytotoxicity as immunoconjugates with the anti-transferrin receptor monoclonal antibody 5E9.

The N-substituted hydrazine bifunctional compounds contain a hydrazine moiety, and a reactive pyridinyldithio or ortho-nitrophenyldithio moiety. These novel bifunctional compounds may be used to link a variety of molecules to form useful conjugates. The molecule to be linked to the hydrazine moiety of the bifunctional compound contains a free carbonyl group, or a group that is derivatized to contain a carbonyl group, such as a cytotoxic reagent molecule. When the molecule containing the carbonyl group is linked to the hydrazine moiety of the bifunctional compound a hydrazone bond is formed which is a semicarbazone, carbazone, thiosemicarbazone, carboxylatehydrazone or arylhydrazone bond, depending on which bifunctional compound of the invention is used to form the conjugate. The molecule to be linked to the end of the bifunctional compound that contains the pyridinyldithio or ortho-nitrophenyldithio moiety contains a free sulfhydryl group or a group that can be derivatized to contain a sulfhydryl group, such as an antibody molecule or ligand that is preferably reactive with antigens or receptors on the target cells to be killed. The pyridinyldithio moiety leaves during the reaction of the antibody with the bifunctional compound. The molecule containing a free carbonyl group is preferably a cytotoxic reagent molecule such as an anthracycline capable of killing selected cells. In a preferred embodiment, the hydrazone bond linking the cytotoxic reagent molecule to the bifunctional compound permits pH sensitive release of the cytotoxic reagent.

The conjugates of this invention formed by linking molecules with the bifunctional compounds of the invention may be used in pharmaceutical compositions, such as those comprising a pharmaceutically effective amount of at least one immunoconjugate of the invention and a pharmaceutically acceptable carrier. The present invention also encompasses methods for the selective delivery of cytotoxic reagents to a selected population of target cells desired to be eliminated, as well as methods for treating a mammal in a pharmaceutically acceptable manner with a pharmaceutically effective amount of the compositions of the invention.

Advantageously, the compounds, conjugates, pharmaceutical compositions, and methods disclosed herein provide a useful approach to the targeting of cytotoxic reagents to a selected population of cells for the preferential killing of those target cells in the treatment of diseases such as cancers and other tumors, non-cytocidal viral or other pathogenic infections, and autoimmune disorders.

DETAILED DESCRIPTION OF THE INVENTION

Figure 1:
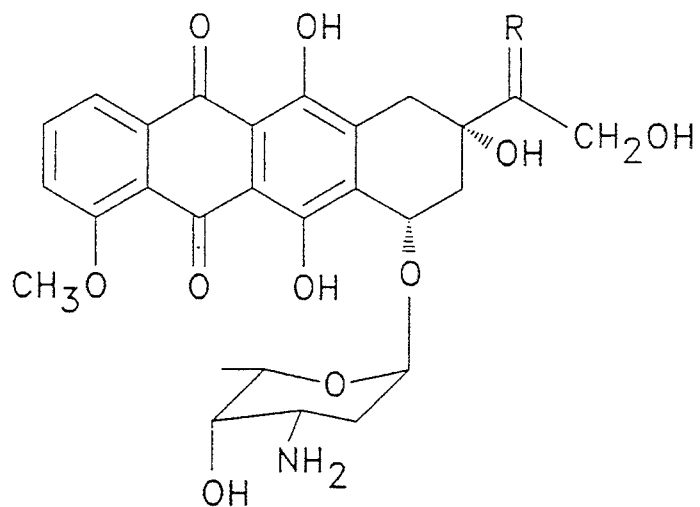
FIG. 1 depicts the structures of the novel adriamycin derivatives of the invention formed by reacting the bifunctional compounds of the invention with adriamycin as described in Examples 1–5, infra.
Figure 1:
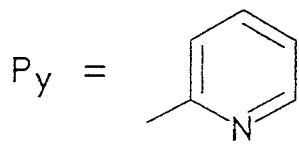
Figure 1:
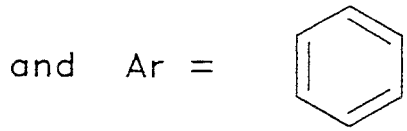

In order that the invention herein disclosed may be more fully understood, the following detailed description is set forth.

The present invention relates to novel N-substituted hydrazine bifunctional compounds: N-[2-[(2-pyridinyl)-dithio]-ethyl]hydrazinecarboxamide (compound 10); 2-[[[2-[(2-pyridinyl)dithio]-ethyl]amino]carbonyl]carbonic dihydrazide (compound 11a); N-[4-[(2-pyridinyl)-dithio]-2-butenyl]hydrazinecarbothioamide (compound 12); 2-[(2-pyridinyl)dithio]ethyl hydrazinecarboxylate (compound 13); and N-[2-[(2-pyridinyl)dithio]ethyl]-4-hydrazinobenzamide (compound 15). These compounds are used to form novel N-substituted hydrazone derivatives of cytotoxic reagents such as anthracyclines, and when joined to an antibody, to form immunoconjugates. The invention also relates to the methods for production of the bifunctional compounds, cytotoxic derivatives and immunoconjugates, and to pharmaceutical compositions and methods for delivering cytotoxic reagents to target cells to treat diseases such as cancers and other tumors, non-cytocidal viral or other pathogenic infections and autoimmune disorders.

The conjugates comprise at least one cytotoxic derivative molecule connected by one of the bifunctional compounds to at least one molecule that is reactive with the target cell population. This molecule can be a protein such as an antibody, preferably a monoclonal antibody, or a ligand such as bombesin or EGF.

Thus, according to one preferred embodiment, the novel compound, N-[2-[(2-pyridinyl)dithio]ethyl]hydrazinecarboxamide, compound 10, was synthesized and used to form the semicarbazone derivative of ADM containing a semicarbazone bond at the C-13 position of the ADM. In another preferred embodiment, the novel compound 2-[[[2-[(2-pyridinyl)dithio]ethyl]amino]carbonyl] carbonic dihydrazide, compound 11a, was synthesized and used to form the carbazone derivative of ADM having a carbazone bond at the C-13 position of the ADM. According to another preferred embodiment, the novel compound N-[4-[(2-pyridinyl)dithio]-2-butenyl]hydrazinecarbothioamide, compound 12, was synthesized and used to form the thiosemicarbazone derivative of ADM having a thiosemicarbazone bond at the C-13 position of ADM. In yet another preferred embodiment the novel compound 2[(2-pyridinyl)dithio]ethyl-hydrazinecarboxylate, compound 13, was synthesized and used to form the hydrazone derivative of ADM having a carboxylate-hydrazone bond at the C-13 position of the ADM. In still another preferred embodiment, the novel compound, N-[2-[(2-pyridinyl)dithio]ethyl]-4-hydrazinobenzamide, compound 15, was used to form the arylhydrazone derivative of ADM having an arylhydrazone bond at the C-13 position of ADM.

In other embodiments the invention relates to conjugates containing at least one molecule reactive with a target cell population, such as an antibody or ligand, and at least one cytotoxic molecule that kills cells, linked by the novel bifunctional compounds of the invention. Thus, according to another preferred embodiment, the invention relates to immunoconjugates containing an antibody directed against a target cell population, for example a tumor cell population, the antibody having a number of anthracycline derivative molecules linked to its structure. The anthracycline derivative molecules are attached to a thiolated antibody covalently such that a disulfide bond is formed between each drug molecule and an antibody, the bifunctional compound being attached to the anthracycline derivative by a hydrazone bond at the C-13 position of the anthracycline. More than one drug molecule may be attached to each antibody molecule using one bifunctional compound of the invention per drug molecule. A molar ratio of 4:1 indicates that 4 drug (i.e. anthracycline derivative) molecules are attached to a single antibody.

In an alternative embodiment, the anthracycline derivative is reduced to create a sulfhydryl group and this ADM derivative is condensed with a maleimide-modified antibody forming a thioether bond between the antibody and the anthracycline.

These conjugates permit the pH-sensitive release of unmodified anthracycline drug to prevent structural modifications of the drug that might result in reduction of cytotoxicity.

In yet another preferred embodiment, the invention encompasses anthracycline-ligand conjugates comprised of a ligand, such as a polypeptide or peptide ligand, that reacts with one or more receptors associated with the cell surface of a target cell population, the ligand having at least one anthracycline derivative molecule linked to its structure. The anthracycline is covalently bound to the peptide by a bifunctional compound that is attached to the anthracycline at the C-13 position of the anthracycline via a hydrazone bond. In an alternative embodiment, the anthracycline derivative is reduced to create a sulfhydryl group and this derivative is then condensed with a maleimide-modified ligand.

The conjugates of this invention can be prepared in a stepwise fashion by the initial formation of a novel N-substituted hydrazine compound that is used to form a hydrazone derivative of the cytotoxic reagent which is then reacted with a protein or ligand of the appropriate specificity (see Hardy, "Purification And Coupling Of Fluorescent Proteins For Use In Flow Cytometry" in *Handbook Of Experimental Immunology*, Volume 1: Immunochemistry, D. M. Weir et al. (Eds.), pp. 31.4–31.12 (4th Ed. 1986) for a discussion of conventional antibody coupling techniques and Varga et al., supra, for the preparation of ligand conjugates).

The length of the bifunctional compound that connects the cytotoxic reagent with the cell-reactive component of the conjugates may vary as long as the bifunctional compound is attached via one of the afore-mentioned hydrazone bonds to the carbonyl group of the cytotoxic reagent molecule or molecules.

The cytotoxic reagents that comprise the conjugates of this invention may be any molecule containing a carbonyl group. Such reagents include, but are not limited to, the anthracyclines: adriamycin, daunomycin, detorubicin, carminomycin, idarubicin, epirubicin, esorubicin, 4'-THP-adriamycin, AD-32, and 3'-deamino-3'-(3-cyano-4-morpholinyl)-doxurubicin (Casazza, "Experimental Studies On New Anthracyclines", in *Adriamycin: Its Expanding Role In Cancer Treatment*, M. Ogawa et al. (Eds.), pp. 439–52 (Excerpta Medica, 1984)).

It is to be understood that the cell-reactive molecule to which the cytotoxic reagent is linked in the conjugate via the bifunctional compound can be any molecule that binds to or reacts with the cell population sought to be eliminated and which possesses a sulfhydryl group or can be modified to contain a sulfhydryl or maleimide group. Such molecules include, but are not limited to, large molecular weight proteins (generally, greater than 10,000 daltons) such as antibodies, smaller molecular weight proteins (generally, less than 10,000 daltons), polypeptide or peptide ligands, and non-peptidyl ligands.

Antibodies that comprise the immunoconjugates of this invention may be any antibody reactive with a specific target cell population desired to be eliminated or killed. Examples of such antibodies include, but are not limited to, antibodies that bind to tumor-associated antigens such as antigens found on carcinomas, melanomas, lymphomas, bone or soft tissue sarcomas, as well as other tumors, antibodies that bind to virus- or other pathogen-associated antigens, and antibodies that bind to abnormal cell surface antigens. These antibodies may be polyclonal or preferably, monoclonal, and can be produced using techniques well established in the art (DeWeger et al., Eradication Of Murine Lymphoma And Melanoma Cells By Chlorambucil-Antibody Complexes", *Immunological Rev.* 62:29–45 (1982) (tumor-specific polyclonal antibodies produced and used in conjugates); Yeh et al., "Cell Surface Antigens Of Human Melanoma Identified By Monoclonal Antibody," *Proc. Natl. Acad. Sci.* 76:2927–31 (1979), and Brown et al., "Structural Characterization Of Human Melanoma-Associated Antigen p97 With Monoclonal Antibodies," *J. Immunol.* 127 (No.2):539–46 (1981) (tumor-specific monoclonal antibodies produced)). For example, the monoclonal antibody, L6, specific for human lung carcinoma cells or the monoclonal antibody, 791T/36, specific for osteogenic sarcoma cells, can be used. Furthermore, non-internalizing or preferably, internalizing antibodies may be used. The term "antibody" as used in this application includes intact antibody molecules or fragments containing the active binding region of the antibody molecule, e.g., Fab or F(ab')$_2$. If monoclonal antibodies are used, the antibodies may be of, but are not limited to, mouse or human origin, or chimeric antibodies.

It is also to be understood the term "ligand" as used herein includes any molecule that binds specifically to a receptor associated with the cell surface of a target cell population. Preferred ligands that can be used to form the anthracycline-ligand conjugates of this invention include, but are not limited to, protein, polypeptide, or peptide ligands such as transferrin, epidermal growth factor (EGF), bombesin, gastrin, gastrin-releasing peptide, platelet-derived growth factor, IL-2, IL-6, tumor growth factors (TGF)-α and TGF-β, vaccinia growth factor (VGF), insulin and insulin-like growth factors I and II. Other non-peptidyl ligands include steroids, carbohydrates and lectins.

Thus, the cell-reactive "targeting" molecule, e.g., antibody or ligand, of the conjugates of this invention acts to deliver the cytotoxic reagent molecules to the particular target cell population with which the antibody or ligand is reactive. For example, an antibody directed against an antigen found on the surface of tumor cells will bind to and deliver the cytotoxic reagents to those tumor cells or an antibody directed against a protein of the Human Immunodeficiency Virus (HIV) that causes AIDS will deliver its cytotoxic reagents to HIV-infected cells. Similarly, because tumor cells, such as carcinomas, preferentially express certain receptors at high density, such as the EGF receptor, a ligand such as EGF will bind to and deliver the cytotoxic reagent to carcinoma cells.

Release of the cytotoxic reagent within or at the site of the particular cell population with which the antibody or ligand reacts results in the preferential killing of those particular cells. Thus, it is apparent that the conjugates of this invention are useful in the treatment of any disease wherein a specific cell population is sought to be eliminated, the cell population having a cell surface antigen or receptor which allows binding of the conjugate. Diseases for which the present conjugates are useful include, but are not limited to, cancers and other tumors, non-cytocidal viral or other pathogenic infections such as AIDS, herpes, CMV (cytomegalovirus), EBV (Epstein Barr Virus), and SSPE (subacute schlerosis panencephalitis), and rheumatoid arthritis.

Without being bound by theory, it is believed that the antibody- or ligand-linked cytotoxic reagent molecules, i.e., in the form of the conjugates of the invention, are delivered to the target cells to be killed via the antibody or ligand specificity and may then enter the cell via the same endocytic pathway that leads to internalization of membrane-bound unconjugated antibodies and ligands (Pastan et al., "Pathway Of Endocytosis", in *Endocytosis*, I. Pastan et al. (Eds.), pp. 1–44 (Plenum Press, 1985)). Once inside the cell, the endocytic vesicles containing the conjugate fuse with primary lysosomes to form secondary lysosomes (Embleton et al., supra, at p. 334). Because the cytotoxic molecules are bound to the antibody or ligand component of the conjugate via acid-sensitive hydrazone bonds, exposure of the conjugate to the acid environment of the endocytic vesicles and lysosomes results in the release of the cytotoxic reagent from the conjugate. Furthermore, the reagent released is believed to be in the form of a relatively unmodified reagent capable of full cytotoxic activity. Thus, the acid-sensitive bond of the conjugate is highly advantageous for the release of the cytotoxic reagent within target cells, enhancing the cytotoxicity of the conjugate toward those cells. Alternatively, the hydrazone bond may be cleaved under acidic and reducing conditions in the immediate environment external to or surrounding the target cells, e.g., at the site of a tumor, and the released drug may be taken up by the tumor cells.

The novel bifunctional compounds, derivatives of cytotoxic reagents and Conjugates of the invention, and methods for their production, are exemplified by preferred embodiments in which the anthracycline, adriamycin, was used. In general, carbonyl derivatives of adriamycin were prepared by treating adriamycin hydrochloride with one of the five bifunctional compounds of the invention in methanol at room temperature. It was found that addition of catalytic amounts of trifluoroacetic acid (TFA) accelerated the condensation reactions so that the reaction was complete after an overnight stirring. Few side-products were produced in these reactions and the purification procedure only required precipitation with acetonitrile. These simplified procedures represent an improvement over those previously reported by Greenfield et al., supra, in that they are easier to perform, more economical, and faster, and provide additional, novel bifunctional compounds for conjugating a variety of molecules.

Figure 2:
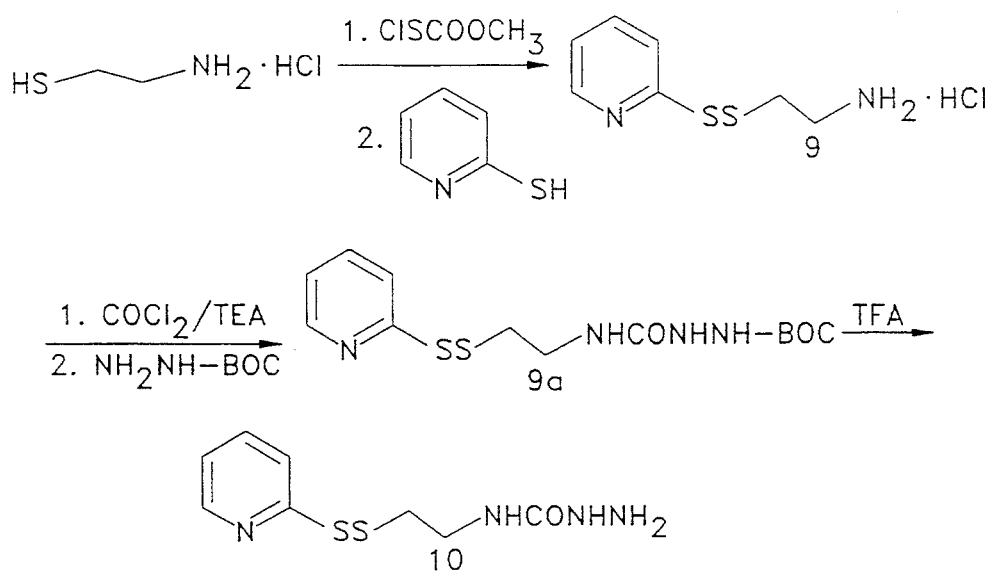
FIG. 2 depicts in schematic form the synthesis of the N-[2-[(2-pyridinyl)dithio]ethyl]hydrazinecarboxamide bifunctional compound used to prepare the semicarbazone derivative of adriamycin as described in Example 1, infra.

In a first embodiment, a novel bifunctional compound was prepared by first reacting methoxycarbonylsulfenyl chloride with 2-aminoethanethiol hydrochloride, then 2-mercaptopyridine to form 2-[(2-pyridinyl)dithio]ethanamine hydrochloride (see FIG. 2). This compound was then reacted with phosgene in the presence of triethylamine (TEA), then t-butyl carbazate, to form N-[2-[(2-pyridinyl)dithio]ethyl]-2-(tert.-butoxy-carbonyl)hydrazinecarboxamide. The hydrazinecarboxamide was next dissolved in TFA to form N-[2-[(2-pyridinyl)dithio]ethyl]hydrazinecarboxamide, compound 10, a semicarbazide, which was then reacted with adriamycin hydrochloride to form the semicarbazone derivative of ADM containing a reactive pyridinyldithio moiety, compound 1, FIG. 1.

Figure 3:
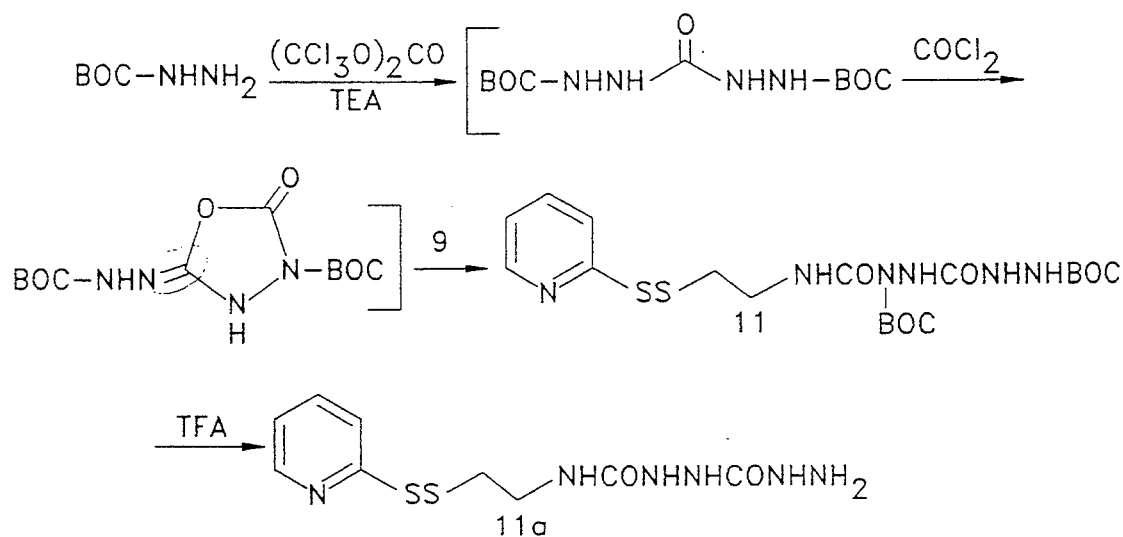
FIG. 3 depicts in schematic form the synthesis of the 2-[[[2-[(2-pyridinyl)dithio]ethyl]amino]carbonyl] carbonic dihydrazide bifunctional compound used to prepare the carbazone derivative of adriamycin as described in Example 2, infra.

In another preferred embodiment, a novel carbazide bifunctional compound was prepared (FIG. 3). The compound t-butyl carbazate was reacted with triphosgene in the presence of TEA. 2-(2-pyridinyldithio)ethanamine hydrochloride was then added to form 2-[[[2-[(2-pyridinyl)dithio]ethyl]amino]carbonyl]-2,2'-bis(tert.-butoxycarbonyl) carbonic dihydrazide. This intermediate was added to TFA to form 2-[[[2-[(2-pyridinyl)- dithio]ethyl]amino]carbonyl]carbonic dihydrazide, compound 11a, which was then added to adriamycin hydrochloride to form the carbazone derivative of ADM (compound 2, FIG. 1) containing a reactive pyridinyldithio moiety.

Figure 4:
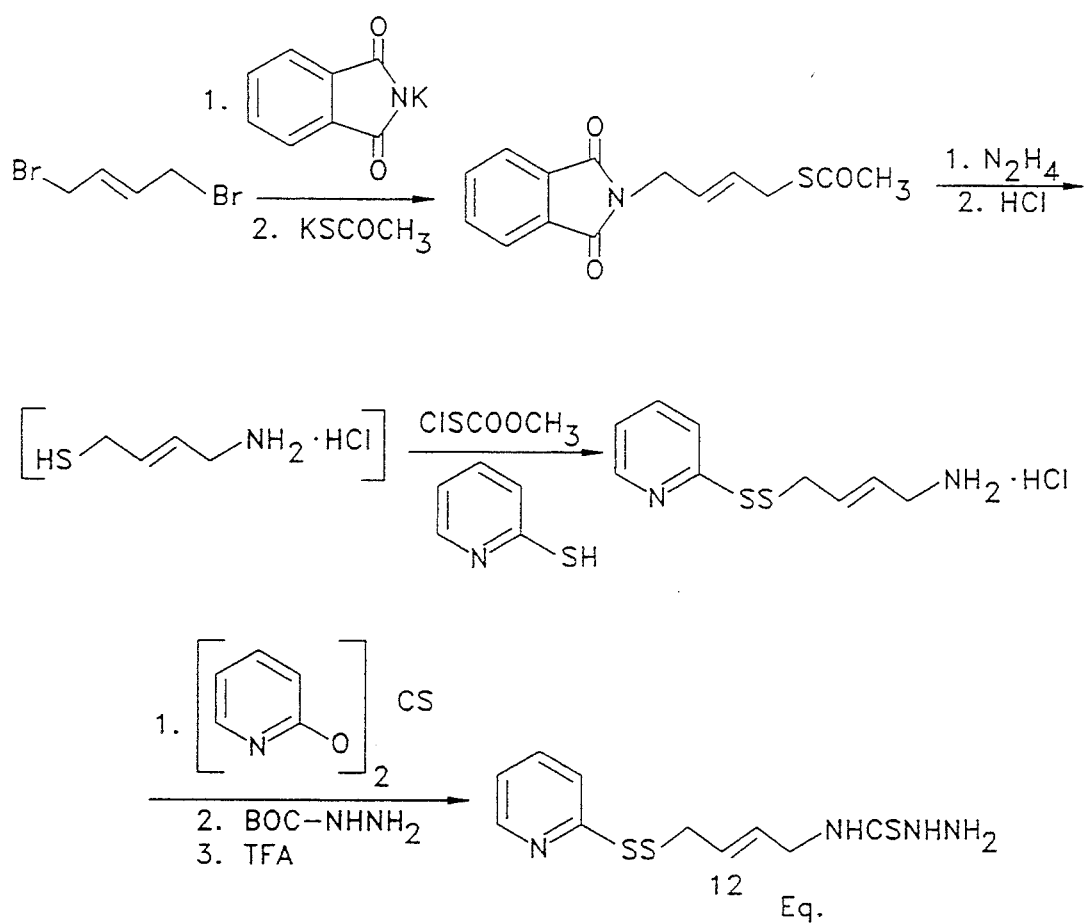
FIG. 4 depicts in schematic form the synthesis of the N-[4-[(2-pyridinyl)dithio]-2-butenyl]hydrazinecarbothioamide bifunctional compound used to prepare the thiosemicarbazone derivative of adriamycin as described in Example 3, infra.

In yet another preferred embodiment, a novel thiosemicarbazide bifunctional compound was formed (FIG. 4). In this embodiment, potassium phthalimide was reacted with 1,4-dibromo-2-butene to form 1-bromo-4-(N-phtalimido)-2butene. This compound was reacted with potassium thioacetate to form 1-(acetylthio)-4-(N-phthalimido)-2-butene which was then reacted with hydrazine and was treated with methoxycarbonylsulfenyl chloride followed by 2-mercaptopyridine to form 1-amino-4-[(2-pyridinyl)dithio]-2-butene hydrochloride. This compound was combined with TEA followed by di-2-pyridyl thionocarbonate, then t-butyl carbazate was added to form the t-boc derivative of N-[4-[(2-pyridinyl)dithio]-2-butenyl]-hydrazinecarbothioamide, compound 12. This compound was dissolved in TFA to form a compound in the form of a gum, which was then reacted with adriamycin hydrochloride and TFA to form the thiosemicarbazone derivative of ADM having a thiosemicarbazone bond at the C-13 position of the ADM (compound 3, FIG. 1) and having a reactive pyridinyldithio moiety.

Figure 5:
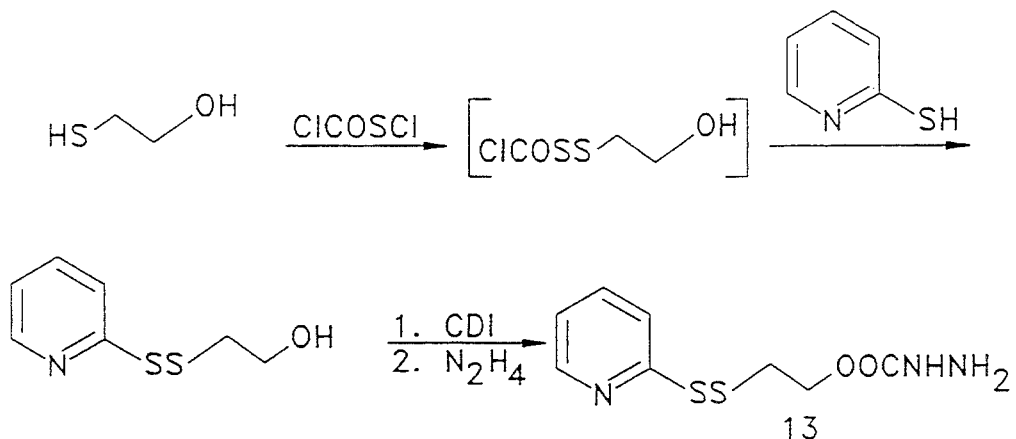
FIG. 5 depicts in schematic form the synthesis of the 2[(2-pyridinyl)dithio]ethyl hydrazinecarboxylate bifunctional compound used to prepare the carboxylatehydrazone derivative of adriamycin as described in Example4, infra.

Another preferred embodiment involves the formation of yet another novel bifunctional compound (FIG. 5). Chlorocarbonyl sulfenyl chloride was reacted with 2-mercaptoethanol and 2-mercaptopyridine. Ammonium carbonate solution was added to form 2-(2-Pyridinyl)dithio)ethanol as a colorless oil. Carbonyldiimidazole was added and the mixture was reacted with hydrazine to form 2-[(2-pyridinyl)dithio]ethyl hydrazinecarboxylate, compound 13. This compound was reacted with adriamycin hydrochloride and TFA and then acetonitrile to form the carboxylatehydrazone derivative of ADM (compound 4, FIG. 1) having a carboxylatehydrazone bond at the C-13 position of the ADM and having a reactive pyridinyldithio moiety.

Figure 6:
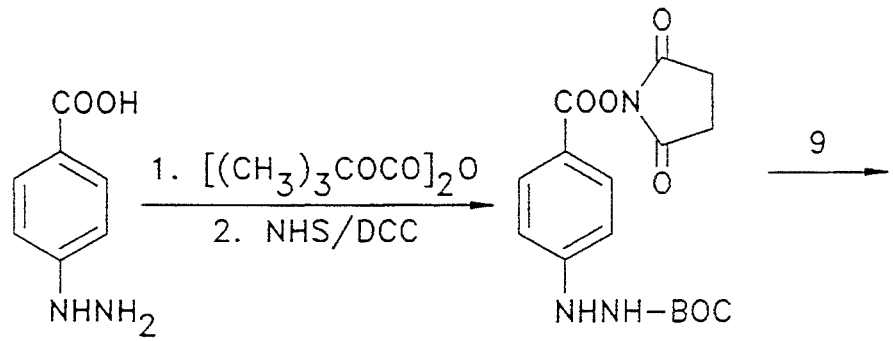
FIG. 6 depicts in schematic form the synthesis of the N-[2-[(2-pyridinyl)dithio]ethyl]-4-hydrazinobenzamide bifunctional compound used to prepare the arylhydrazone derivative of adriamycin as described in Example 5, infra.
Figure 6:
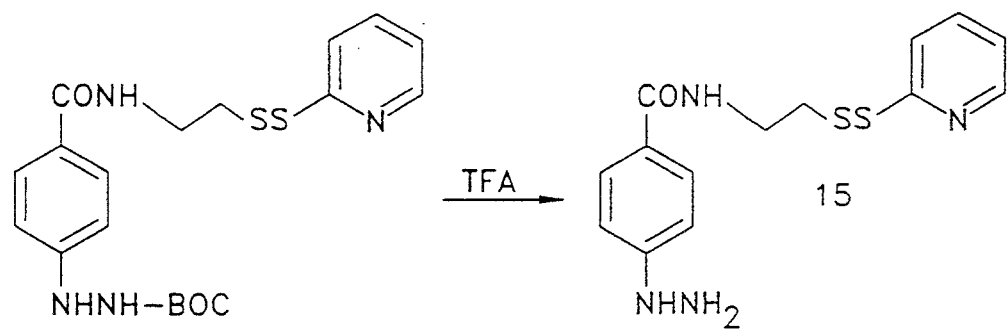

In still another preferred embodiment a novel bifunctional compound was synthesized (FIG. 6). This compound was prepared by reacting p-hydrazinobenzoic acid with di-t-butylpyrocarbonate to form 4-(N-boc-hydrazino)benzoic acid. This compound was reacted with N-hydroxysuccinimide and DCC to give the N-hydroxysuccinimide ester of 4-N-boc-(hydrazino) benzoic acid. This material was reacted with 2-(2-pyridinyl)dithio)ethanamine hydrochloride and TEA to form N-[2-(2-pyridinyl)dithio]ethyl-4-N-boc-(hydrazino)benzamide. This compound was then treated with TFA to form N-[2-[(2-pyridinyl)dithio]ethyl]-4-hydrazinobenzamide, compound 15, which was then reacted with adriamycin hydrochloride to form the arylhydrazone derivative of ADM (compound 5, FIG. 1) having an arylhydrazone bond at the C-13 position of ADM and having a reactive pyridinyldithio moiety.

Figure 7:
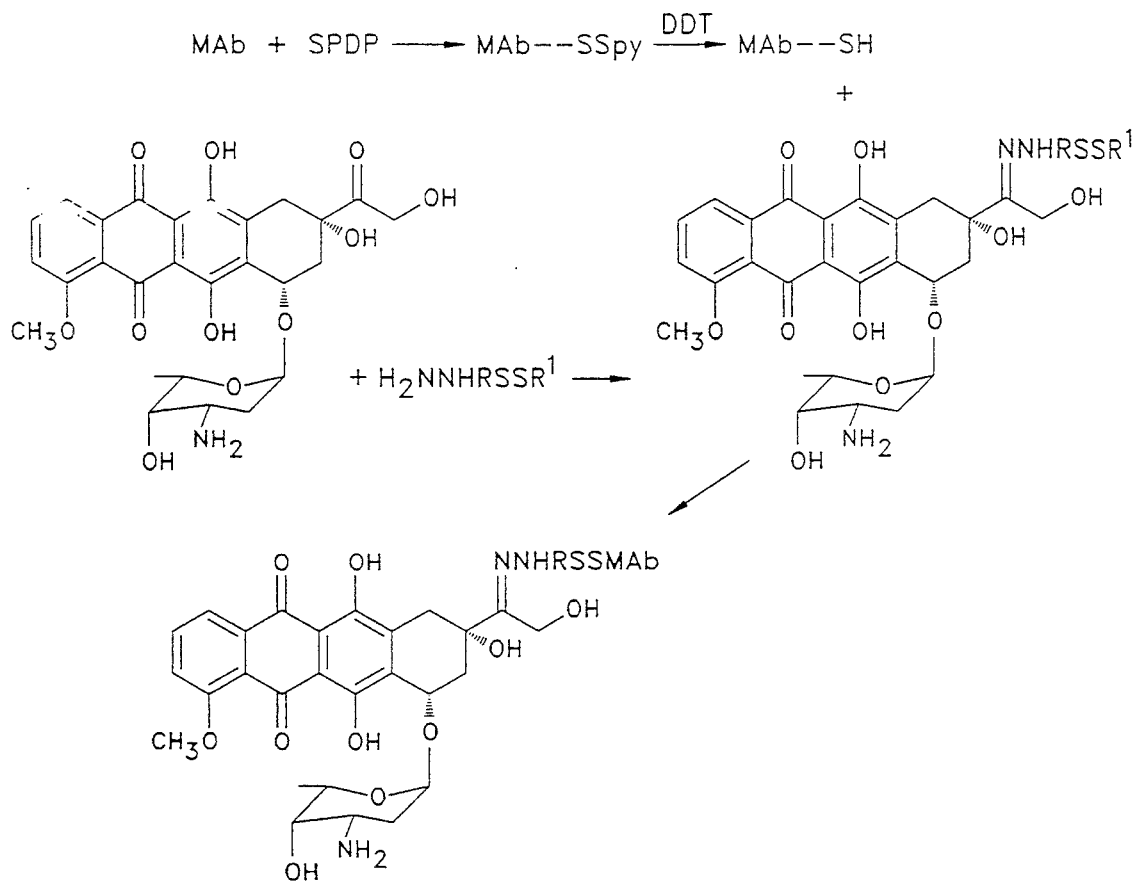
FIG. 7 depicts in schematic form the preparation of immunoconjugates of the invention using an antibody thiolated with SPDP reacted with the bifunctional compounds of the invention, as described in Example 7, infra.
Figure 7:
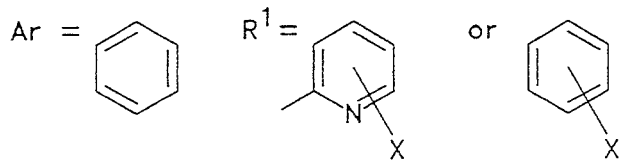
Figure 8:
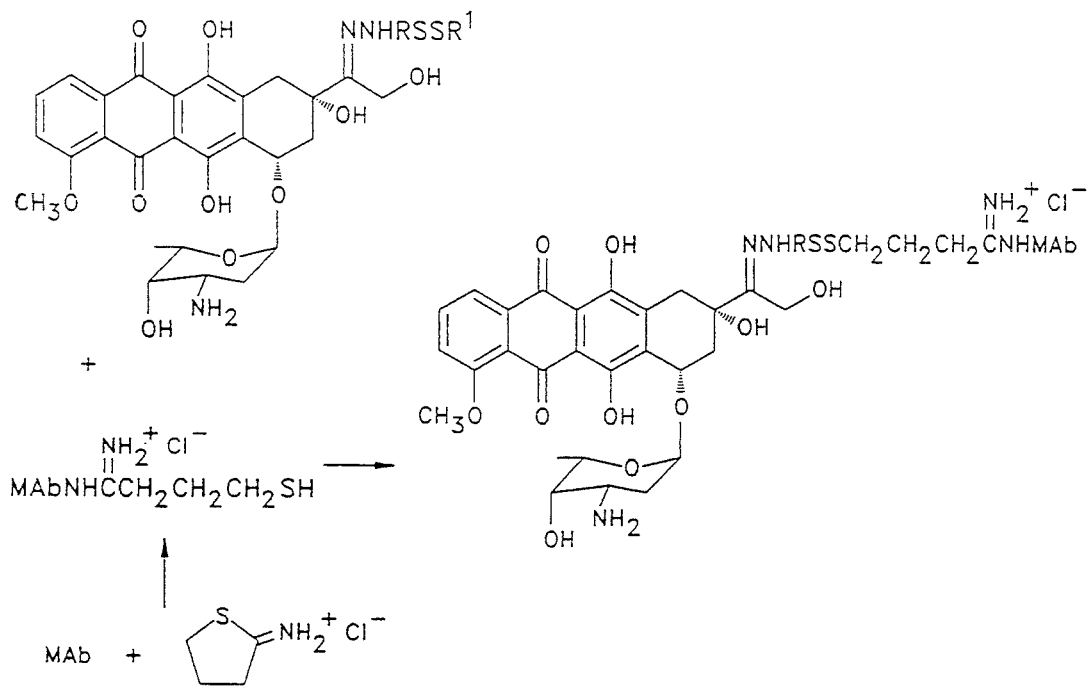
FIG. 8 depicts in schematic form the preparation of immunoconjugates of the invention using an antibody thiolated with 2-IT reacted with the bifunctional compounds of the invention.
Figure 8:
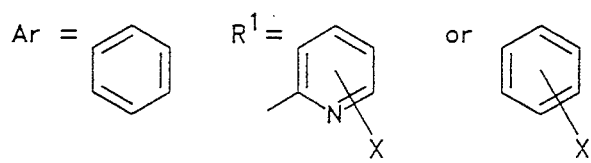

The novel N-substituted hydrazone derivatives of ADM described above were used to form the conjugates of the invention. Each derivative was reacted with a monoclonal antibody that had been previously thiolated with SPDP or with 2-IT (2-iminothiolane) as shown in FIGS. 7 and 8, respectively. The resulting immunoconjugates were comprised of ADM molecules conjugated to the monoclonal antibody by means of the bifunctional compound attached to the C-13 position of each ADM molecule through a hydrazone bond. The bifunctional compounds also contained a disulfide bond through which each was attached to the antibody.

The bifunctional compound connecting the ADM and the antibody may be comprised of a number of constituents and linkages as long as these linkages include an acid-sensitive hydrazone bond at the C-13 position of the anthracycline. The antibody of the preferred embodiments was monoclonal antibody 5E9.

Figure 9:
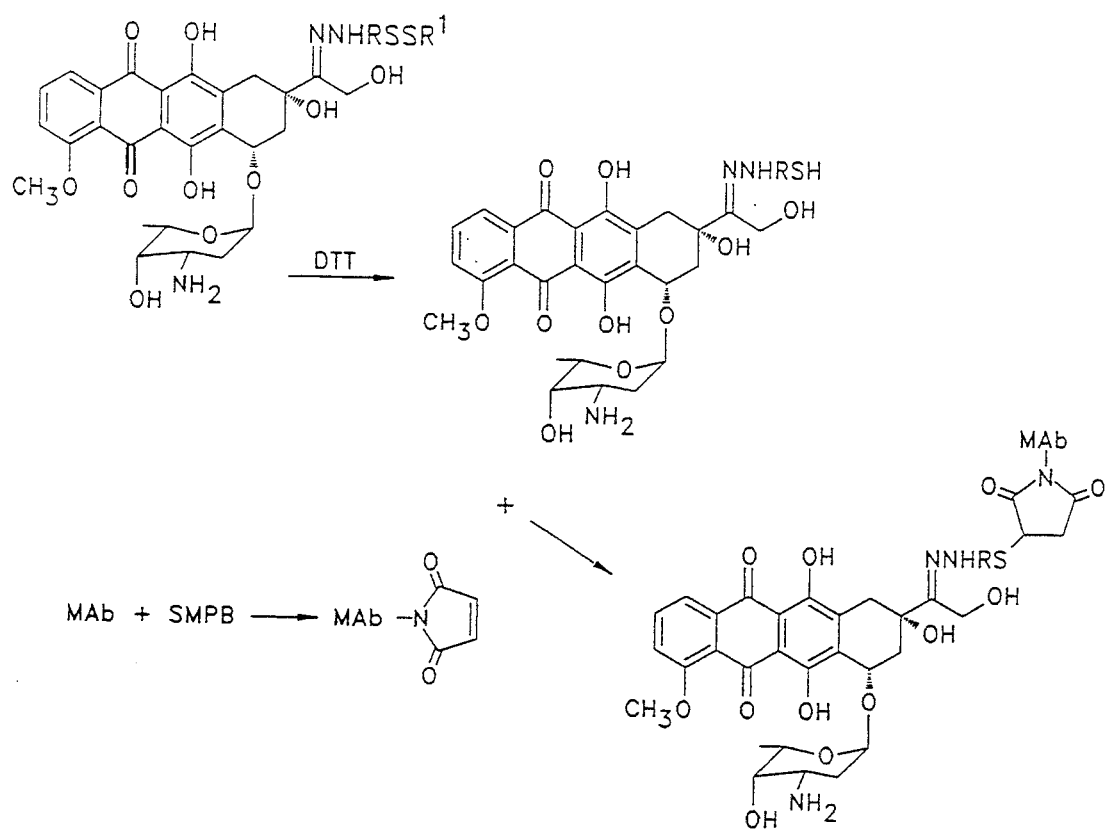
FIG. 9 depicts in schematic form the preparation of immunoconjugates of the invention having a thioether linkage between the antibody and the reduced bifunctional compound using a antibody reacted with SMPB to add maleimide groups.
Figure 9:
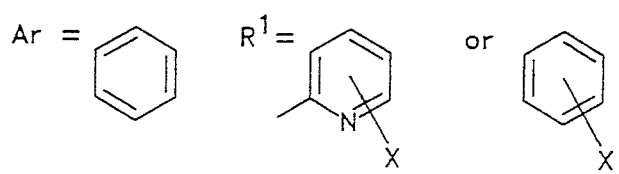

In another embodiment of the invention, the novel bifunctional compounds are combined with adriamycin to form a derivative which is then further treated with the reducing agent dithiotreitol (DTT) or tributylphosphine, to produce an adriamycin derivative containing a sulfhydryl (-SH) group at the end of the bifunctional compound. This derivative is then reacted with a monoclonal antibody or ligand to which maleimide groups have been attached, for example, by reaction of the antibody with succinimidyl-4-(p-maleimidophenyl) butyrate (SMPB). An immunoconjugate is formed that has a bifunctional compound attached by a hydrazone bond at the C-13 position of each ADM and has a thioether linkage as part of the attachment to the antibody (see FIG. 9).

Thus, it is apparent that the bifunctional compound connecting the ADM and antibody or ligand may be comprised of a number of constituents and linkages as long as these linkages include a hydrazone bond at the 13-keto position of the ADM and a reactive pyridinyldithio or orthonitrophenyldithio group for connecting to the antibody.

According to another embodiment, the novel ADM derivatives of the invention are reacted with a ligand such as bombesin, EGF or transferrin, the ligand having first been derivatized to possess thiol groups or maleimide groups. In the case of bombesin, a cysteine residue is introduced onto the amino terminus of the peptide to provide a reactive sulfhydryl group for conjugation with the ADM derivative. In the case of murine EGF, the polypeptide is reacted with SPDP to introduce a reactive sulfhydryl group at the amino terminus of the molecule for conjugation. In the case of transferrin, the protein is first reacted with 2-IT to introduce reactive thiol groups onto the protein structure. In each case, the thiolated ligand is then reacted with the ADM derivative to form an anthracycline-ligand conjugate of the invention having a bifunctional compound between the ligand and the ADM, the bifunctional compound being attached to the C-13 position of each anthracycline molecule via a hydrazone bond.

It is apparent that the present invention provides novel hydrazone derivatives of anthracyclines having the following general formula I:

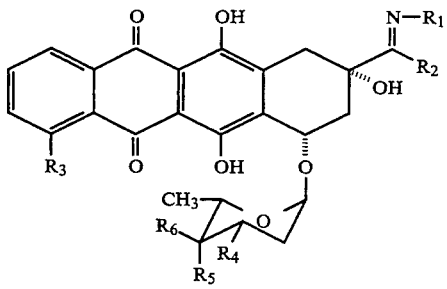

wherein:
R$_1$ is NHCONH(CH$_2$)$_n$SSR$_8$; NHCONHNHCONH(CH$_2$)$_n$SSR$_8$; NHCSNH(CH$_2$)$_m$CH=CH(CH$_2$)$_n$SSR$_8$; NHCOO(CH$_2$)$_n$SSR$_8$; NHArCONH(CH$_2$)$_n$SSR$_8$; NCONH(CH$_2$)$_n$S—H; NCONHNHCONH(CH$_2$)$_n$S—H; NHCSNH(CH$_2$)$_m$CH=CH(CH$_2$)$_n$S—H; NHCOO(CH$_2$)$_n$S—H; or NHArCONH(CH$_2$)$_n$S—H;
wherein R$_8$ is

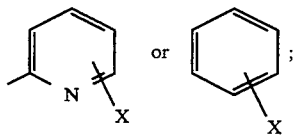

X is H, NO$_2$ or Halogen;
Ar is

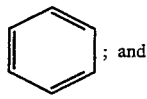 ; and m, n are integers from 1 to 10, which may be the same or different;
R$_2$ is CH$_3$, CH$_2$OH, CH$_2$OCO(CH$_2$)$_3$CH$_3$, or CH$_2$OCOCH(OC$_2$H$_5$)$_2$;
R$_3$ is OCH$_3$, OH or hydrogen;
R$_4$ is NH$_2$, NHCOCF$_3$, 4-morpholinyl, 3-cyano-4-morpholinyl, 1-piperidinyl, 4-methoxy-1-piperidinyl, benzyl amine, dibenzyl amine, cyanomethyl amine or 1-cyano-2-methoxyethyl amine;
R$_5$ is OH, O—THP or hydrogen; and
R$_6$ is OH or hydrogen, provided that R$_6$ is not OH when R$_5$ is OH or O—THP.
and formula II:

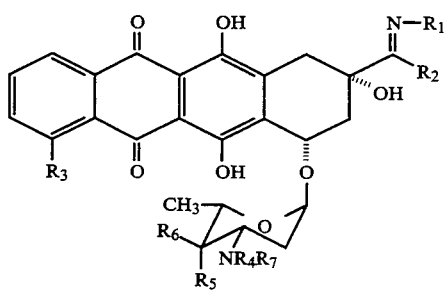

wherein:
R$_1$ is NHCONH(CH$_2$)$_n$SSR$_8$; NHCONHNHCONH(CH$_2$)$_n$SSR$_8$;
NHCSNH(CH$_2$)$_m$CH=CH(CH$_2$)$_n$SSR$_8$; NHCOO(CH$_2$)$_n$SSR$_8$; NH-Ar-CONH(CH$_2$)$_n$SSR$_8$; NHCONH(CH$_2$)$_n$S—H; NHCONHNHCONH(CH$_2$)$_n$S—H; NHCSNH(CH$_2$)$_m$CH=CH(CH$_2$)$_n$S—H; NHCOO(CH$_2$)$_n$S—H or NH—Ar—CONH(CH$_2$)$_n$S—H
wherein R$_8$ is

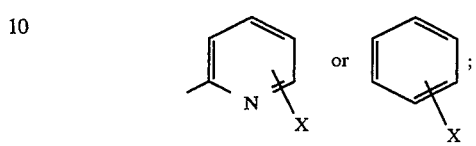

X is H, NO, or halogen;
Ar is

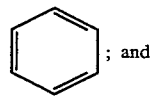 ; and m, n are integers from 1 to 10, which may be the same or different;
R$_2$ is CH$_3$, CH$_2$OH, CH$_2$OCO(CH$_2$)$_3$CH$_3$, or CH$_2$OCOCH(OC$_2$H$_5$)$_2$;
R$_3$ is OCH$_3$, OH or hydrogen;
R$_4$ and R$_7$ are independently hydrogen, alkyl, substituted alkyl, cycloalkyl, substituted cycloalkyl, aryl, substituted aryl, aralkyl or substituted aralkyl; or R$_4$, R$_7$ and N together form a 4–7 membered ring, wherein said ring may be optionally substituted;
R$_5$ is OH, O—THP or hydrogen; and
R$_6$ is OH or hydrogen, provided that R$_6$ is not OH when R$_5$ is OH or O—THP.

The above-disclosed bifunctional compounds and N-substituted hydrazone derivatives of anthracycline are novel compounds. The hydrazone derivatives of anthracycline may be used as novel cytotoxic reagents and also represent intermediates in the preparation of the novel conjugates of the invention. The hydrazone derivatives of anthracycline are exemplified by adriamycin semicarbazone; adriamycin carbazone; adriamycin thiosemicarbazone; adriamycin carboxylatehydrazone and adriamycin arylhydrazone, respectively, as described in the preferred embodiments discussed herein.

As can be seen from the above formulae, the N-substituted hydrazone ADM derivatives of the invention include N-substituted hydrazones of any of a number of known anthracyclines such as adriamycin, daunomycin and carminomycin. In addition, the derivatives include N-substituted hydrazones derivatized at specific sites on the anthracycline structure (e.g., 4'-THP-adriamycin hydrazone and 3'-deamino-3'-(3-cyano-4-morpholinyl-)adriamycin hydrazone). These latter derivatives can be synthesized by first derivatizing the anthracycline to form a desired analog and then using that analog to prepare the N-substituted hydrazone derivatives of the invention. Known anthracycline analogs include those described in U.S. Pat. Nos. 4,464,529 and 4,301,277 (3'-deamino-3'-(4-morpholinyl) or 3'-deamino-3'(3-cyano-4-morpholinyl) anthracycline analogs), U.S. Pat. Nos. 4,202,967 and 4,314,054 (3'-deamino-3'-(1-piperdinyl) or 3'-deamino-3'-(4-methoxy-1-piperdinyl) anthracycline analogs), U.S. Pat. No. 4,250,303 (N-benzyl or N,N-dibenzyl anthracycline analogs), U.S. Pat. No. 4,591,637 (N-methoxymethyl or N-cyanomethyl anthracycline analogs) and U.S. Pat. No. 4,303,785 (acetal analogs of anthracyclines). Thus, these known anthracycline analogs can be reacted as described hereinabove to produce novel hydrazone derivatives of ADM which can then be conjugated to a cell-reactive molecule, such as an antibody or ligand of a desired specificity, as described above.

Alternatively, an underivatized N-substituted hydrazone derivative of this invention can first be produced as described herein from the underivatized anthracycline, such as adriamycin, daunomycin or carminomycin, and this novel derivative can then be derivatized to produce a novel N-substituted hydrazone substituted as desired. For example, the semicarbazone ADM derivative can be derivatized at its amino sugar moiety by reductive amination with 2,2'-oxydiacetaldehyde using the procedure described in U.S. Pat. No. 4,464,529, to produce the semicarbazene of '3-deamino-3'-(4-morpholino) anthracycline. In addition, the N-substituted hydrazone derivatives can be derivatized at the $R_5$ position of formulae I and II, as described in U.S. Pat. No. 4,303,785 to produce acetal derivatives of the hydrazone such as 4'-THP-ADM N-substituted hydrazone.

It should be understood that these procedures for derivatizing the hydrazones of the invention can use as starting materials N-substituted hydrazones of other reagents, including various chemotherapeutic agents. And, anthracyclines other than ADM, such as daunomycin or carminomycin, may be used to produce novel compounds such as [N-benzyl daunomycin N-substituted hydrazone or 3'-deamino-3'(4-morpholinyl)-carminomycin N-substituted hydrazone and other compounds using the other derivatives, which are also within the scope of this invention.

The anthracycline derivatives of the present invention were evaluated for release rates of the drug adriamycin at pH values of 4.5, 5.0 and 7.4 and exhibited a wide range of release rates. In addition, the immunoconjugates comprising the derivatives conjugated to a monoclonal antibody were evaluated for release of adriamycin at a pH of 4.5. The immunoconjugates were tested for cytotoxicity using Daudi cells in the Inhibition of Colony Formation assay and a correlation between the stability of the hydrazone derivatives was revealed. The immunoconjugates also demonstrated a wide range of release rates and exhibited antibody-directed cell killing (cytotoxicity) for tumor cells in the colony formation assay.

The N-substituted hydrazine compounds of the invention provide useful bifunctional compounds for linking molecules such as targeting and cytotoxic reagents. When used to link cytotoxic molecules containing a carbonyl group, the bifunctional compounds provide an acid-sensitive linkage that is cleaved within a range of pH to release the cytotoxic reagent. The anthracycline immunoconjugates of this invention appear to be an improvement over immunoconjugates reported previously, in which anthracyclines were directly linked to antibodies through the amino sugar portion of the anthracycline, because these amino sugar-linked conjugates often contain lower anthracycline to antibody molar ratios, are less potent than free ADM, and exhibit reduced antibody binding properties (Arnon et al., *Immunological Rev.* 62, supra; Hurwitz et al., *Cancer Res.* 35, supra, and Yamamoto et al., supra). Furthermore, stability studies performed on the immunoconjugates of this invention indicated that the anthracycline was released from the immunoconjugates under acidic conditions similar to those found in a cellular environment. Thus, the immunoconjugates of the present invention may release relatively unmodified drug for delivery to the target cells. The conjugates described herein provide release of drug at a wide range of pH values which may be advantageous for drug delivery.

The bifunctional compounds, immunoconjugates of the invention and the methods for their production are exemplified by preferred embodiments in which derivatives of the anthracycline, adriamycin, were conjugated to the anti-transferrin receptor monoclonal antibody, 5E9.

The present invention also encompasses pharmaceutical compositions, combinations and methods for treating diseases such as cancers and other tumors, non-cytocidal viral or other pathogenic infections, and autoimmune diseases. More particularly, the invention includes methods for treating disease in mammals wherein a pharmaceutically effective amount of at least one anthracycline-containing conjugate is administered in a pharmaceutically acceptable manner to the host mammal.

Alternative embodiments of the methods of this invention include the administration, either simultaneously or sequentially, of a number of different conjugates, i.e., bearing different cytotoxic reagents or different antibodies or ligands, for use in methods of combination chemotherapy. For example, an embodiment of this invention may involve the use of a number of anthracycline-immunoconjugates wherein the specificity of the antibody component of the conjugate varies, i.e., a number of immunoconjugates are used, each one having an antibody that binds specifically to a different antigen or to different sites or epitopes on the same antigen present on the cell population of interest. The anthracycline component of these immunoconjugates may be the same or may vary. For example, this embodiment may be especially useful in the treatment of certain tumors where the amounts of the various antigens on the surface of a tumor is unknown or the tumor cell population is heterogenous in antigen expression and one wants to be certain that a sufficient amount of drug is targeted to all of the tumor cells at the tumor site. The use of a number of conjugates bearing different antigenic or epitope specificities for the tumor increases the likelihood of obtaining sufficient drug at the tumor site. Additionally, this embodiment is important for achieving a high degree of specificity for the tumor because the likelihood that normal tissue will possess all of the same tumor-associated antigens is small (cf Hellstrom et al., "Monoclonal Antibodies to Two Determinants of Melanoma-Antigen p97 Act Synergistically In Complement-Dependent Cytotoxicity", *J. Immunol.*, 127 (No. 1) pp. 157–160 (1981)).

Alternatively, a number of different immunoconjugates can be used, wherein only the anthracycline component of the conjugate varies. For example, a particular antibody can be linked to adriamycin to form one immunoconjugate and can be linked to daunomycin to form a second immunoconjugate. Both conjugates can then be administered to a host to be treated and will localize, due to the antibody specificity, at the site of the selected cell population sought to be eliminated. Both drugs will then be released at that site. This embodiment may be important where there is some uncertainty as-to the drug resistance of a particular cell population such as a tumor because this method allows the release of a number of different drugs at the site of or within the target cells. An additional embodiment includes the conjugation of more than one type of anthracycline to a particular antibody to form an immunoconjugate bearing a variety of different anthracycline molecules along its surface, all linked to the antibody via a 13-keto hydrazone bond. Administration of the immunoconjugate of this embodiment results in the release of a number of different drugs at the site of or within the target cells. Furthermore, a combination of anthracycline-ligand conjugates can be used wherein the drug can be targeted to a cell population carrying a specific antigen as well as a receptor for a specific ligand on its surface. Again, one type of anthracycline or a number of different drugs can be used in this combination therapy.

The conjugates of the invention can be administered in the form of pharmaceutical compositions using conventional modes of administration including, but not limited to, intravenous, intraperitoneal, oral, intralymphatic, or administration directly into the site of a selected cell population such as a tumor. Intravenous administration is preferred. In the case of the immunoconjugates, for in vivo treatment, it may be useful to use conjugates comprising antibody fragments such as Fab or F(ab')2 or chimeric antibodies.

The pharmaceutical compositions of the invention comprising the conjugates may be in a variety of dosage forms which include, but are not limited to, solid, semi-solid and liquid dosage forms such as tablets, pills, powders, liquid solutions or suspensions, suppositories, polymeric microcapsules or microvesicles, liposomes, and injectable or infusible solutions. The preferred form depends upon the mode of administration and the therapeutic application.

The pharmaceutical compositions may also include conventional pharmaceutically acceptable carriers known in the art such as serum proteins such as human serum albumin, buffer substances such as phosphates, water or salts or electrolytes.

The most effective mode of administration and dosage regimen for the conjugate compositions of this invention depends upon the severity and course of the disease, the patient's health and response to treatment and the judgement of the treating physician. Accordingly, the dosages of the conjugates and any accompanying compounds should be titrated to the individual patient. Nevertheless, an effective dose of the anthracycline immunoconjugate of this invention may be in the range of from about 1 to about 100 mg/m$^2$ anthracycline or from about 500–5000 mg/m$^2$ antibody. An effective dose of the anthracycline-ligand conjugates may be in the range of from about 1 to about 100 mg/m$^2$ anthracycline or from about 1 to about 100 mg/m$^2$ ligand.

In order that the invention described herein may be more fully understood, the following examples are set forth. It should be understood that these examples are for illustrative purposes only and are not to be construed as limiting the scope of this invention in any manner.

EXAMPLES

Preparation of Bifunctional Compounds and Derivatives of Adriamycin (ADM)

Melting points (MP) were determined on a Fisher-Johns (Medford, Mass.) melting point apparatus and are uncorrected. Nuclear Magnetic Resonance (NMR) spectra were obtained on a Brucker AM 300 instrument. Infrared (IR) spectra were run as KBr pellets or CHCl$_3$ solutions on a P-E FTIR (Fourier Transformation Infrared) instrument (Norwalk, Conn.), model 1800. MS (mass spectrum) and HRMS (high resolution mass spectrum) were obtained with Kratos MS25RFA and MS50TC instruments (Manchester, England), respectively. Flash chromatography was performed using Woelm (Atlanta, Ga.) silica gel (silica 32–63). Thin Layer Chromatography (TLC) was carried out on Analtec (Newark, Del.) silica gel GHLF plates or RPS-F reversed phase plates, both 250 microns. For routine High Pressure Liquid Chromatography, (HPLC), a P-E pump, series 4 LC, a HP 1046A fluorescence detector and a Phenomenex (Torrance, Calif.) IB Sil-5C18 (150×4.6 mm) column were used. The mobile phase was a 70:30 methanol-phosphate buffer (50 mmol ammonium phosphate, pH 4.4) at a flow rate of 1.5 ml/min. For release-rate measurements the HPLC system comprised of two Waters pumps model 510, an auto-sampler model 712 and a gradient controller model 680. Chromatography was performed on a Waters C-18 column and the mobile phase was a 68:32 mixture of triethylammonium formate buffer (0.05M, Ph 2.8) and acetonitrile, respectively. The fluorescence of the eluted adriamycin was detected by using an ABI Fluorescence Detector model 980 (excitation, 254 nm; emission, 550 nm) obtained from Applied Biosystems, Ramsey, N.J. Acetate buffer was used for pH 4.5 and 5.0; phosphate saline buffer was used for pH 7.4. Adriamycin-HCl was obtained from Sanraku Inc. (Japan). All other chemicals were obtained from commercial sources. Elemental analyses were performed in the analytical department of Bristol-Myers Squibb Company, Wallingford, Conn. and at Oneida Research Services.

EXAMPLE 1

Preparation of Bifunctional Compound 10 and Semicarbazone Derivative of ADM

The following example describes a method for producing a bifunctional compound and a semicarbazone derivative of ADM having a semicarbazone bond at the C-13 position of ADM. In this example, N-[2-[(2-pyridinyl)dithio)ethyl]hydrazinecarboxamide, compound 10, is prepared by the reaction sequence shown in FIG. 1. Reacting cysteamine hydrochloride with methoxycarbonylsulfenyl chloride followed by 2-mercaptopyridine gave 2-(2-pyridinyl)dithioethanamine hydrochloride (compound 9 in FIG. 1). This in turn was reacted with phosgene and t-butyl carbazate followed by trifluoroacetic acid (TFA) to give the desired product (compound 10).

Preparation of 2-[(2-pyridinyl)dithio]ethanamine hydrochloride

A solution of methoxycarbonylsufenyl chloride (Zumach et al., Agnew Chem. International Edit. 9:54–63 (1970), (6.33 g, 50 mmol) in HPLC grade methanol (100 ml) was stirred under N$_2$ and chilled in ice. To this a solution of 2-aminoethanethiol hydrochloride (5.7 g, 50 mmol) in methanol (50 ml) was added dropwise. After the addition was complete, the solution was stirred at room temperature (RT) for 2 h. The solvent was then evaporated and the residual oil crystallized from acetone (100 ml) to yield a solid (6.9 g). This solid was dissolved in methanol (100 ml). The solution was chilled in ice, stirred under N$_2$ and treated dropwise with a solution of 2-mercaptopyridine (3.82 g, 34 mmol) in methanol (50 ml). The solution was stirred for 1 h at RT, concentrated to small volume and diluted slowly with acetone until crystallization occurred. After 1 h in the refrigerator the solid was collected by filtration, and dried to yield the compound 2-[(2-pyridinyl)dithio]ethanamine hydrochloride (compound 9). This compound has been described by Field et al., *J. Org. Chem.* 29:1632–1635 (1964) and Connor and Schroit, *Biochem.* 27:848–851 (1988)). The compound was characterized as follows: mp 123°–5° (5.8 g, 52%) . IR (KBr) 2952, 2913, 1610, 1575, 1559, 1451, 1115, 767 cm$^{-1}$. NMR ($D_2O$). δ 8.46, 7.83, 7.34 (d, m, m 4H, Py), 3.37 (t, 2H $CH_2CH_2NH_2$), 3.12 (t, 2H, $SCH_2CH_2$). MS(m/e): 187 (corresponds to [M+H]+) 170, 152, 142 , 112 , 104 , 76 .

Analysis: calculated for $C_7H_{11}CLN_2S_2.\frac{1}{4}H_2O$: C, 37.00, H, 5.06, N, 12.33. Found: C, 36.82: H, 4.99, N, 12.37.

Preparation of N-[2-[(2-pyridinyl)dithio]ethyl ]-2-(tert.-butoxycarbonyl)hydrazinecarboxamide 2-[(2-pyridinyl)dithio]ethanamine hydrochloride (2.22 g, 10 mmol) was suspended in dry methylene chloride (100 ml) and treated with triethylamine (TEA) (5.8 ml). This solution was added dropwise to an ice cold stirred solution of phosgene (10 ml of a 1.93M toluene solution) in methylene chloride (200 ml). The reaction was monitored by TLC and when no more starting material was present, $N_2$ was passed throughout the mixture for a while. Then t-butyl carbazate (1.32 g, 10 mmol) was added and the mixture left to stir overnight. The solution was washed with water and the solvent evaporated. The residue was chromatographed over silica using methylene chloride:methanol (100:2) solvent system. The appropriate fractions were combined to yield 1.74 g of N-[2-[(2-pyridinyl)dithio]ethyl]-2-(tert-butoxycarbonyl) hydrazinecarboxamide(compound 9a) as a foam, characterized as follows: IR (KBr) 3281, 2979, 2932, 1723, 1672, 1577, 1560, 1545, 1448, 1419, 1253, 1161, 762 cm$^{-1}$. NMR($CDCl_3$) δ 8.50, 7.56, 7.51, 7.12 (4H, Py), 3.51 (2H, $CH_2$), 2.89 (2H, $CH_2S$), 6.84, 6.37, 6.17 (3H, NH), 1.44 (9H), $(CH_3)_3C$). MS(m/e) 345 (corresponds to [M+H]+), 317, 289, 245, 213, 178, 134, 112.

Preparation of N-[2-[(2-pyridinyl)dithio]-ethyl]hydrazine-carboxamide

N-[2-[(2-pyridinyl)dithio]ethyl]-2-(tert-butoxycarbonyl)hydrazinecarboxamide (570 mg, 1.66 mmol) was dissolved in ice cold TFA (10 ml). The solution was stirred in ice for 10 min and additional 10 min without cooling. The excess of TFA was evaporated under reduced pressure as much as possible and the residue chromatographed over silica using a methylene-chloride:methanol:concentrated ammonium hydroxide (100:5:0.5) solvent system. The appropriate fractions were combined according to TLC and the solvent evaporated to leave a crystalline residue (0.42 g, quantitative). An analytical sample was prepared by crystallizing from IPA, mp 105°–7°. N-[2-[(2-pyridinyl)dithio]ethyl]hydrazinecarboxamide (compound 10) was characterized as follows: IR(KBr) 3336, 3220, 3064, 2949, 2934, 1670, 1623, 1575, 1562, 11–33, 1452, 1369, 1172, 1046, 770 cm$^{-1}$. NMR($CD_3OD$) δ 8.41, 7.78, 7.21 (4H, Py), 3.43 (2H, $NCH_2$), 2.91 (2H $SCH_2$). MS(m/e) 245 (corresponds to [M+H]+0, 221, 213, 162, 134, 112.

Analysis: Calculated for $C_8H_{12}N_4OS_2$: C, 39.32, H, 4.95; N, 22.93; S, 26.24. Found, C 39.19; H, 4.86; N, 22.48; S, 25.02.

Preparation of the semicarbazone derivative of adriamycin hydrochloride and N-[2-[(2-pyridinyl)dithio]ethyl]hydrazinecarboxamide Compound 10 (0.37 g, 1.5 mmol) in methanol (25 ml) was added to a stirred suspension of adriamycin hydrochloride (0.66 g, 1.14 mmol) in methanol (50 ml). TFA (5 drops) was added and the mixture left to stir overnight. The clear solution was concentrated and chromatographed over a C-18 column using methanol:water (60:40) containing 0.3% ammonium acetate, as solvent system. The appropriate fractions were combined and the methanol evaporated as much as possible. The aqueous phase was freeze-dried and the residue dissolved in methanol and added to acetonitrile. The red solid was collected by centrifugation, and dried. (0.65 g, 68%). The semicarbazone derivative of ADM was characterized as follows: IR(KBr) 3399, 2976, 2936, 1671, 1618, 1578, 1538, 1417, 1286, 1210, 1117, 1015, 989, 764cm$^{-1}$. NMR($CD_3OD$) δ 8.25, 7.76, 7.62, 7.48, 7.07 (py, ph, H), 4.95 (anomeric H), 4.63 ($CH_2OH$), 4.24 ($CH_3CH$), 3.97 ($OCH_3$), 3.5–2.9 (cluster absorption of $SSCH_2$, —$CH_2$—, $CH_2$—NH), 1.29 (HC—$CH_3$). MS(m/e) 770 (corresponds to [M+H]+), 641, 437,346. HRMS: calculated $C_{35}H_{40}N_5O_{11}S_2$: 770. 2166; Found: 770.2157.

EXAMPLE 2

Preparation of Bifunctional Compound 11a and the Carbazone Derivative of ADM

The following example describes a method for producing a carbazide bifunctional compound and the carbazone derivative of ADM having a carbazone bond at the C-13 position of ADM. In this example, the reaction shown in FIG. 2 and described in Example 1 between 2-[(2-(pyridinyl)dithio]ethanamine hydrochloride and t-butyl carbazate was started with t-butyl carbazate and triphosgene, as shown in FIG. 3, to yield a bifunctional compound, (compound 11a), a carbazide. In this case, excess t-butyl carbazate was reacted with phosgene to give the carbonic dihydrazide.

Preparation of 2-[[[2-[(2-pyridinyl)dithio]ethyl]amino]-carbonyl]-2,2'-bis(tert.-butoxycarbonyl) carbonic dihydrazide t-butyl carbazate, (0.396 g, 3 mmol) was dissolved in dry chloroform (10 ml). The solution was stirred under $N_2$ at RT and TEA was added (0.6 g, 6 mmol). This was followed by the addition of triphosgene (0.296 g, 1 mmol) all at once. A vigorous reaction ensued and when it subsided, 2-(2-pyridinyldithio)ethanamine hydrochloride (0.667 g, 3 mmol) in chloroform containing TEA (0.3 g, 3 mmol) was added. The mixture was stirred at RT for 1½ h then washed with water (3×20 ml) dried and the solvent evaporated under reduced pressure to leave a foam (0.91 g). This material was chromatographed over silica using methylene chloride:-methanol (100:2) solvent system. The fractions were monitored by TLC and combined accordingly to yield the compound 2-[[[2-[(2-pyridinyl)dithio]ethyl]amino]-carbonyl]-2,2'-bis(tert.-butoxycarbonyl) carbonic dihydrazide (compound 11) as a foam (0.54 g, 52%). Compound 11 was characterized as follows: IR(KBr)3302, 2980, 2933, 1726, 1683, 1498, 1252, 1160, 1047, 1018, 763 cm$^{-1}$. NMR($CDCl_3$) δ 8.50, 7.57, 7.49, 7.10, (d,q,d,t, 4H, Py), 3.52 (t, 2H, $SSCH_2$) 2.90 (t, 2H $CONCH_2$), 1.46 [$C(CH_3)_3$], 8.30, 6.50, 6.29 (b,s,s, NH). MS (m/e) 503 (corresponds to [M+H]+), 447, 431, 419, 403, 347, 303, 213, 179, 112.

Preparation of 2-[[[2-[(2-pyridinyl)dithio]ethyl]amino]carbonyl]carbonic dihydrazide Compound 11 (0.34 g, 0.68 mmol) was stirred for 10 min with ice cold TFA (5 ml) and an additional 10 min without cooling. The TFA was evaporated as much as possible and the residue was chromatographed over silica using methylene chloride:methanol:concentrated $NH_4OH$ (100:5:0.5) solvent system. The appropriate fractions were combined and after evaporation compound 11a was obtained as a hygroscopic foam (0.2 g, quantitative yield). Compound 11a was characterized as follows: IR (film) 3330, 2964, 2929, 1698, 1660, 1576, 1486, 1231, 1045, 759 cm$^{-1}$. NMR (CDCl$_3$) δ 8.50, 7.56, 7.10 (d, m, m, 4H, Py), 3.52 (q, 2H, CH$_2$N), 2.91 (t, 2H, CH$_2$SS), 8.87, 8.85, 4.19, 3.78 (D$_2$O exchangeable protons, NH). MS (m/e) 303 (corresponds to [M+H]$^+$), 213, 112.

Preparation of the carbazone derivative of adriamycin hydrochloride and 2-[[[2-[(2-pyridinyl)dithio]ethyl]amino]carbonyl]carbonic dihydrazide Adriamycin hydrochloride (356 mg, 0.6 mmol) and compound 11a (0.2 g, 0.68 mmol) were left to stir overnight in methanol (50 ml) containing 2-3 drops of TFA. A clear solution was obtained and HPLC (methanol: 0.01M ammonium phosphate solution, pH 4.5, 70:30 solvent system) indicated that over 90% of the adriamycin had been converted to the semicarbazone. The solvent was therefore evaporated and the residue chromatographed over a C-18 column using a solvent system of methanol:water (60:40) and containing 0.3% ammonium acetate. The fractions were monitored by reversed phase TLC (same solvent system but 3% ammonium acetate) and/or HPLC and fractions free of adriamycin were combined. Most of the methanol was evaporated under reduced pressure. The aqueous solution was freeze-dried and the red residue was dissolved in a small volume of methanol. The solution was filtered and added to stirred acetonitrile (1 L). The clear solution was concentrated to about a third of its volume and the solid obtained was collected by centrifugation and dried to give the carbazone of ADM (Compound 4) (160 mg). A second crop (85 mg) was obtained by concentrating the solution to 100 ml, diluting with ether and collecting the solid by centrifugation (total yield 49%). This carbazone derivative was characterized as follows: IR(KBr): 3346, 2975, 2936, 1711, 1668, 1618, 1578, 1286, 1210, 1083, 1015, 765 cm$^{-1}$. NMR(CD$_3$OD) δ 8.43, 7.89, 7.77, 7.52, 7.21, (Py, phenyl H), 5.15 (anomeric H) 4.57 (CH$_2$OH), 4.25 (CH$_3$CH), 3.99 (OCH$_3$), 3.53 (SSCH$_2$), 3.17 (—CH$_2$—, ring), 3.05 (CH$_2$NN=), 2.38 (—CH$_2$—, ring) 1.29 (CHCH$_3$). MS(m/e) 828 (corresponds to [M+H]$^+$), 699, 572, 537, 377, 346, 289, 213.

EXAMPLE 3

Preparation of Bifunctional Compound 12 and the Thiosemicarbazone Derivative of ADM This example describes the preparation of a bifunctional compound, compound 12, and the thiosemicarbazone derivative of ADM having a thiosemicarbazone bond at the C-13 position of ADM. In this example, the thio analog of the semicarbazide described above in Example 1 (compound 10) was prepared as shown diagrammatically in FIG. 4. When using 2-[(2-pyridinyl)dithio]ethanamine, an elimination of 2-mercaptopyridine was observed which could be ascribed to the increased nucleophilicity of the thiosemicarbazide moiety in the penultimate product stage. This problem was circumvented by employing the trans-2-butene group as shown in FIG. 4.

Preparation of 1-bromo-4-(N-phtalimido)-2-butene

To a solution of 1,4-dibromo-2-butene (8.4 g, 40 mmol) in DMF (200 ml) was added potassium phthalimide (4.62 g 24 mmol) portionwise during 1 h. After stirring overnight, the solvent was evaporated and the residue partitioned between water and methylene chloride. The organic layer was washed several times with water, dried and the solvent evaporated. The residue was crystallized from 2-propanol yielding the desired product 1-bromo-4-(N-phtalimido-2-butene) (3.95 g, 59%); characterized as follows: mp 101°-2°. IR(KBr) 1775, 1711, 1466, 1436, 1393, 723 cm$^{-1}$. NMR (CDCl$_3$) δ 7.81, 7.73 (m, m 4H, phenyl), 5.88, 5.81 (m, m 2H, 2 =CH—) 4.30 (d, 2H CH$_2$—N), 3.90 (d, 2H CH$_2$Br). MS (m/e) 280 (corresponds to [M+H]$^+$), 200.

Analysis: Calculated for $C_{12}H_{10}BrNO_2$: C, 51.45; H, 3.60; N, 5.00. Found: C, 52.35; H, 3.47, N, 4.80.

Preparation of 1-(acetylthio)-4-(N-phthalimido)-2-butene

A mixture of 1-bromo-4-(N-phthalimido)-2-butene (3.95 g; 14 mmol) and potassium thioacetate (1.77 g, 15.5 mmol) in absolute ethanol (50 ml) was heated to reflux for ½ h. The solvent was evaporated and the residue was extracted with methylene chloride. The solvent was evaporated to yield a crystalline residue (3.85 g, 99%) which was used as such for the next step. An analytical sample was prepared by crystallization from 2-propanol, mp 69°-71°. This compound was characterized as follows: IR(KBr) 1769, 1713, 1688, 1427, 1391, 1114, 958 cm$^{-1}$. NMR (CDCl$_3$) δ 7.80, 7.73 (m, m 4H Ph), 5.70 (m, 2H, 2 =CH—), 4.24 (d, 2H, CH$_2$N), 3.48 (t, 2H CH$_2$S), 2.29 (s, 3H, C—CH$_3$). MS (m/e) 276 (corresponds to [M+H]$^+$), 234, 200.

Analysis: Calculated for $C_{14}H_{13}NO_3S$: C, 61.07; H, 4.76; N, 5.09. Found: C, 61.29; H, 4.82, N,5.21.

Preparation of 1-amino-4-[(2-pyridinyl)dithio]-2-butene hydrochloride

A solution of 1-acetylthio-4-(N-phtalimido)-2-butene (6.5 g, 23.6 mmol) in absolute ethanol (150 ml) and hydrazine (1.74 g, 54 mmol) was heated to reflux. The reaction was followed by TLC and when no starting material was present the solution was chilled in ice and treated with 6N HCl (10 ml). A voluminous precipitate formed and was identified as phtalhydrazide (NMR, MS) and it was filtered off. The filtrate was concentrated to 10 ml and diluted with water. The solid was filtered off and the filtrate was washed with ether (2×) and methylene chloride (1×), filtered through Celite and freeze-dried. The solid was dissolved in a small amount of methanol and the solution was filtered through Celite, the solvent evaporated and the residue evacuated overnight. A waxy, hygroscopic material was obtained, having the characteristics of: NMR (DMSO-D$_2$O) δ 5.83, 5.60 (m, m 2H, 2=CH—) 3.40 (d, 2H CH$_2$NH$_2$), 3.16 (d 2H, CH$_2$SH) MS (m/e) 104 (corresponds to [M+H]$^+$), 87, 70. This waxy material was dissolved in HPLC grade methanol (75 ml). The solution was stirred and treated with methoxycarbonylsulfenyl chloride (3 g, 23.7 mmol). After ½ h starting material was not detected by TLC. The solvent was evaporated and the residue was redissolved in methanol (75 ml). The solution was stirred and treated with 2-mercaptopyridine (2.7 g, 24 mmol). After 2 h the solvent was evaporated and the residue evacuated at high vacuum. The residue was then dissolved in a mixture of 0.01N HCl and methanol (90:10, 130 ml). The cloudy solution was washed with methylene chloride, filtered through Celite and freeze-dried to yield 1-amino-4-[(2-pyridinyl)dithio]-2-butene hydrochloride as a highly hygroscopic fluffy material (4 g, 68%) having the characteristics of IR(KBr) 3433, 2959, 2884, 1607, 1576, 1447, 1418, 1118, 767 cm$^{-1}$. NMR(D$_2$O) δ 8.51, 8.13, 8.02, 7.54 (m 4H, Py) 5.87, 572 (m, m 2H, 2 =CH—) 3.54 (d 2H, CH$_2$NH$_2$) 3.43 (d 2H, CH$_2$S). MS (m/e) 213 (corresponds to [M+H]$^+$), 196, 112.

Preparation of N-[4-[(2-pyridinyl)dithio]-2-butenyl]hydrazinecarbothioamide 1-amino-4- [(2-pyridinyl) dithio]-2-butene hydrochloride (1.5 g., 6 mmol) was suspended in stirred methylene chloride (30 ml). TEA was added (1.46 g, 14.6 mmol) followed by di-2-pyridyl thionocarbonate (Kim and Yi, Tetrahedron Lett. 26:1661–1664 (1985)), (1.4 g, 6 mmol). A clear solution was obtained and TLC showed the absence of starting material. t-Butyl carbazate (0.8 g, 6 mmol) was added and the solution stirred for 1 h. The solution was washed with water and the solvent evaporated. The residue was chromatographed over silica using methylene chloride:methanol (100:2) solvent system and rechromatographed using hexane:ethyl acetate (75:25) solvent system, to yield a foam which is the t-boc derivative of N-[4-[(2-pyridinyl)dithio]-2-butenyl]hydrazinecarbothioamide (1.4 g, 58%), characterized as follows: IR(KBr) 3238, 2971, 2930, 1718, 1544, 1418, 1156, 762 cm$^{-1}$. NMR (CDCl$_3$/D$_2$O) δ 8.43, 7.65, 7.08 (m, m, m 4H, py) 5.57 (m 2H, 2=CH), 4.12 (d 2H, CH$_2$N) 3.45 (d 2H CH$_2$S), 1.46 (s 9H, 3 CH$_3$). MS (m/e) 387 (corresponds to [M+H]$^+$) 355, 287, 276, 112.

The protected carbothioamide (0.86 g, 2.2 mmol) was dissolved in ice cold TFA. The solution was kept in ice for 10 min (under nitrogen) and for an additional 10 min without cooling. The excess acid was evaporated as much as possible at high vacuum and the residue was chromatographed over silica using a methylene chloride:methanol:concentrated NH$_4$OH (100:5:0.5) solvent system. The appropriate fractions were combined to yield compound 12 in the form of a gum (0.39 g, 63%), having the characteristics of: IR(film) 3322, 3198, 2974, 1626, 1574, 1560, 1538, 1448, 1418, 1224, 760 cm$^{-1}$. NMR (CDCl$_3$/D$_2$O) δ 8.41, 7.63, 7.11 (m m m 4H, Py) 5.64 (m 2H, 2=CH), 4.20 (d 2H, CH$_2$N) 3.41 (d 2H, CH$_2$S). MS (m/e) 287 (corresponds to [M+H]$^+$), 225, 221, 144, 112.

Preparation of the thiosemicarbazone derivative of adriamycin hydrochloride and N-[4-[(2-pyridinyl)dithio]-2-butenyl]hydrazinecarbothioamide To a stirred suspension of adriamycin hydrochloride (350 mg, 0.6 mmol) in HPLC grade methanol (50 ml) a solution of compound 12 (350 mg, 1.2 mmol) in HPLC grade methanol (25 ml) was added. TFA (3–4 drops) was added and the mixture was left to stir overnight. A clear solution was obtained and no free adriamycin was detected either by HPLC or TLC. The solution was concentrated to a small volume (5 ml) which was added to acetonitrile (600 ml). A precipitate formed and after cooling in the refrigerator was collected by centrifugation and dried at high vacuum (275 mg, 54%). The thiosemicarbazone derivative was characterized as follows: IR(KB$_r$) 3418, 2934, 1616, 1578, 1534, 1414, 1284, 1208, 1012, 986 cm$^{-1}$. NMR (CD$_3$OD) δ 8.30, 7.80, 7.74, 7.52, (Py, phenyl 7H), 5.60 (2=CH) 5.40 (anomeric H) 4.67 (CH$_2$OH), 4.22 (CH$_3$CH) 4.09 (CH$_2$N) 4.02 (OCH$_3$) 3.5–1.88 cluster absorption including —CH$_2$—SS, —CH$_2$—CH), 1.30 (CH$_3$—CH). MS (m/e) 812 (corresponds to [M+H]$^+$), 701, 683,669, 572,554, 540, 536, 522, 504. HRMS Calculated for C$_{37}$H$_{42}$N$_5$O$_{10}$S$_3$: 812.2094; Found 812.2087.

EXAMPLE 4

Preparation of Bifunctional Compound 13 and the Carboxylatehydrazone Derivative of ADM This example describes the preparation of novel bifunctional compound 13 and the carboxylatehydrazone derivative of ADM. The carboxylatehydrazine bifunctional compound is prepared starting with mercaptoethanol which was derivatized to pyridinyldithioethanol as shown in FIG. 5. This compound was then converted to an activated carbonyl derivative that was condensed with hydrazine.

Preparation of 2[(2-(pyridinyl)dithioethyl hydrazine carboxylate

To a cooled (0° C.) solution of chlorocarbonylsulfeny chloride (1.24 g, 9.45 g mmol) in CH$_2$Cl$_2$ (10 ml) was added dropwise 2-mercaptoethanol, (737 mg, 9.45 mmol). The mixture was stirred for 30 min at 0°–15° C., cooled to 0° C. and treated with a solution of 2-mercaptopyridine (1.05 g, 9.45 mmol) in CH$_2$Cl$_2$ (15 ml). The mixture was stirred at 0° C. for 1 h and then at room temperature for 16 h. After addition of an ammonium carbonate solution (1.0 g in 20 ml H$_2$O), the layers were separated and the organic layer was washed with water, dried, and concentrated in vacuo to give crude 2-(2-pyridinyldithio)ethanol (1.75 g) as a colorless oil. Carbonyldiimidazole (648 mg, 4 mmol) was added to a solution of 2-(2-pyridinyldithio)ethanol (714 mg, 3.8 mmol) in CH$_2$Cl$_2$ (10 ml). The mixture was stirred for 20 h and then cooled to −20° C. and treated with hydrazine (122 mg, 3.8 mmol). The mixture was left standing at −5° C. for 16 h, and then concentrated in vacuo. The residue was chromatographed on silica gel using a methylene chloride:methanol(100:1–3) solvent system to give compound 13, 2-[(2-pyridinyldithio) ethyl hydrazinecarboxylate (340 mg, 37%), as a colorless oil, having the characteristics as follows: NMR (CDCl$_3$) δ 8.46 (1H), 7.62 (2H), 7.08 (1H), 5.92 (1H), 4.35 (t, 2H), 3.70 (s, ZH), 3.01 (t, 2H), 1.56 (s,2H). MS (m/e) 246 (corresponds to [M+H]$^+$), 142, 103.

Preparation of the hydrazone derivative of adriamycin hydrochloride and 2[(2-pyridinyl)dithio]ethyl hydrazinecarboxylate To a suspension of adriamycin hydrochloride (290 mg, 0.5 mmol) in anhydrous methanol (4 ml) were added a solution of compound 13 (170 mg, 6.9 mmol) in methanol (4 ml) and CF$_3$CO$_2$H (6 mg) in methanol (1 ml). After stirring for 24 h the mixture was concentrated to about 4 ml and acetonitrile (50 ml) was added to this solution. The product was isolated by centrifugation. The solid was dissolved in water-methanol and then lyophilized to give the hydrazone derivative of adriamycin, (354 mg, 88%) as a dark red solid, having the characteristics as follows: NMR (CD$_3$OD) δ 8.34 (1H), 7.93 (d, 1H), 7.81 (m, 3H), 7.54 (d, 1H), 7.17 (m, 1H), 5.49 (m, 1H), 5.19 (s, 1H), 4.59 (m,2H), 4.37 (m, 2H), 4.25 (m, 1H), 4.01 (s, 3H), 3.63 (m, 1H), 3.54 (m, 1H), 3.10 (t, 3H), 2.37 (m, 2H), 2.03 (m, 1H), 1.89 (m, 1H), 1.29 (d, 3H). MS (m/e): 771 (corresponds to [M+H]$^+$), 642.

EXAMPLE 5

Preparation of Bifunctional Compound 15 and the Arylhydrazone Derivative of ADM This example describes the method for preparing a novel bifunctional compound, compound 15, and the arylhydrazone derivative of ADM having an arylhydrazone bond at the C-13 position of ADM. Compound 15 is prepared using 4-N-Boc-hydrazinobenzoic acid, and incorporating the 2-(2-pyridinyldithio)ethanamine group as shown in FIG. 6.

4-(N-boc-hydrazino)benzoic acid p-Hydrazinobenzoic acid (760 mg, 5 mmol) was dissolved in dioxane (10 ml), water (5 ml), and 1N NaOH solution (5 ml). Di-t-butylpyrocarbonate (1.31 g, 6 mmol) was added at 0° C. and the reaction mixture was stirred at 0° C. for 1 h and at RT for 30 min. After this period the volume of the solution was reduced to a half and the solution was acidified with 0.5% HCl solution and extracted with EtOAc. The combined EtOAc solution was washed with brine and dried over $Na_2SO_4$. Removal of the solvent gave a slightly brown solid which was recrystallized from EtOAc and hexane (950 mg, 75%), and was characterized as follows: NMR ($CD_3OD$) δ 7.84 (d, 2H, J=8.5 Hz), 6.75 (d, 2H, J=8.5 Hz), 1.48 (s, 9H); IR (KBr) 3316, 1688, 1607, 1298 cm$^{-1}$.

Preparation of N-[2-[(2-pyridinyl)dithio]ethyl-4-(N-boc-hydrazino)benzamide acid 4-(N-boc-hydrazino)benzoic acid (252 mg, 1 mmol) N-hydroxysuccinimide (115 mg, 1 mmol), and dicyclohexyl-carbodiimide (DCC) (247 mg, 1.2 mmol) in N,N-dimethylformamide (DMF) (5 ml) were stirred overnight at room temperature. Dicyclohexylurea (DCU) was filtered off and the filtrate was evaporated. The residue was crystallized by addition of $Et_2O$ to give the N-hydroxysuccinimide ester of 4-(N-boc-hydrazino)benzoic acid (300 mg). This material (250 mg, 0.72 mmol) and 2-(2-pyridinyl)dithio)ethylamine hydrochloride (167 mg, 0.75 mmol) were dissolved in DMF (4 ml). After addition of TEA (0.125 ml, 0.9 mmol), the mixture was stirred overnight at room temperature. DMF was removed and the residue was chromatographed on $SiO_2$ (2% MeOH—$CH_2Cl_2$) to give a foam (217 mg, 52%), having the characteristics as follows: NMR ($CDCl_3$) δ 8.37 (d, 1H, J=5.1 HZ), 8.01 (bt, 1H), 7.78 (d, 2H, J=8.7 Hz), 7.57 (m, 1H), 7.46 (d, 1H, J=8.1 Hz), 7.09 (m, 1H), 6.84 (d, 2H, J=8.7 Hz), 7.40 (bs, 1H), 5.92 (bs, 1H), 3.70 (m, 2H), 2.98 (t, 2H, J=5.8 Hz), 1.45 (s, 9H); IR (KBr) 3303, 1714, 1610, 1505 cm$^{-1}$; ms m/e 421 (M+H), 365, 321, 112, HRMS calculated for $C_{19}H_{25}N_4O_3S_2$ 421.1368, found 421.1358.

Preparation of N-[2-[(2-pyridinyl)dithio]ethyl]-4-hydrazinobenzamide

The previous compound (200 mg, 0.48 mmol) was treated with TFA (1.5 ml) at 0° C. for 1 h. After this period TFA was evaporated and the residue was triturated with $Et_2O$ to give approximately 200 mg of N-[2-[(2-pyridinyl)dithio]-ethyl]-4-hydrazinobenzamide (compound 15) in the form of an oil having the characteristics of: NMR ($CD_3OD$) δ 8.38 (d, 1H, J=4.5 Hz), 7.81 (m, 4H), 7.22 (t, 1H, J=5.8 Hz), 6.97 (d, 2H, J=8.8 Hz), 3.67 (t, 2H, J-6.6 Hz), 3.06 (t, 2H, J=6.6 Hz); IR (film) 3278, 1674, 1613 cm$^{-1}$; MS m/e 321 (M+H).

Preparation of arylhydrazone derivative of adriamycin and N-[2-[(2-pyridinyldithio)ethyl]-4-hydrazinobenzamide Compound 15 and adriamycin hydrochloride (250 mg, 0.43 mmol) were dissolved in MeOH (15 ml) and stirred in the dark for 2 days. The solvent was removed and the residue was chromatographed on C-18 reversed phase $SiO_2$. Elution with MeOH:$H_2O$=2:1 containing 0.3% $NH_4OAc$ gave hydrazone compound 7 as orange powder (30 mg, 8%), having the characteristics as follows: NMR ($CD_3OD$) δ 8.33 (d, 1H, J=4.8 Hz), 7.85 (d, 1H, J=7.9 Hz), 7.74 (t, 1H, J=8.0 Hz), 7.66 (m, 4H), 7.41 (d, 1H, J=8.5 Hz), 7.14 (m, 1H), 7.02 (d, 2H, J=8.8 Hz), 5.46 (bs, 1H), 5.16 (m, 1H), 4.60 (s, 2H), 4.23 (m, 1H), 3.91 (s, 3H), 3.62 (m, 4H), 3.02 (m, 4H), 2.61 (m, 1H), 2.38 (m, 1H), 1.97 (m,2H), 1.32 (d, 3H, J=6.5 Hz); IR (KBr) 3206, 1708, 1607, 1578 cm$^{-1}$; MS m/e 846 (M+H), 737, 717, HRMS calculated for $C_{41}H_{44}N_5O_{11}S_2$, 846.2479, observed 846.2380.

Elution with MeOH:$H_2O$=3:1 containing 0.3% $NH_4OAc$ gave the anhydro derivative as a blue solid (120 mg, 34%). NMR ($CD_3OD$) δ 8.40 (d, 1H, J=4.1 Hz), 7.77 (m, 5H), 7.42 (m, 1H), 7.22 (m, 1H), 7.16 (m, 2H), 5.35 (bs, 1H), 5.26 (m, 1H), 4.65 (s, 2H), 4.00 (m, 1H), 3.93 (s, 3H), 3.67 (t, 2H, J=6.5 Hz), 3.44 (m, 1H), 3.08 (t, 2H, J=6.5 Hz), 2.49 (m, 1H), 1.88 (m, 1H), 1.63 (m, 1H), 1.19 (d, 3H, J=6.5 Hz); MS m/e 828 (M+H) 699, 681, 495; HRMS calculated for $C_{41}H_{41}N_5O_{10}S_2$ 828.2372, observed 828.2300.

EXAMPLE 6

Characterization of the ADM Derivatives

Figure 10:
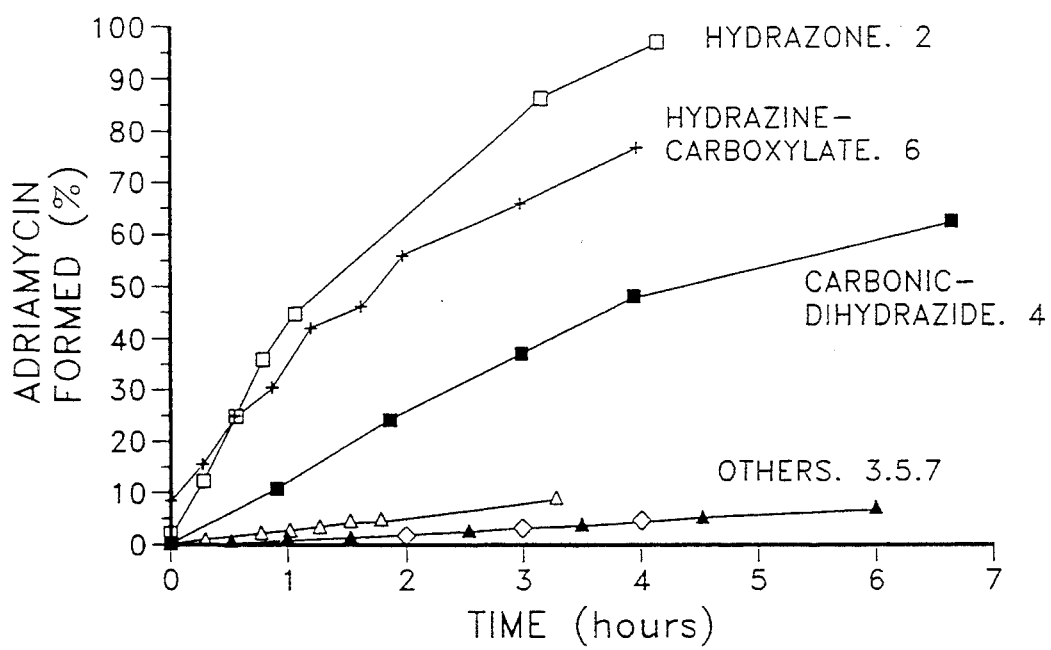
FIG. 10 is a graph of the release of adriamycin as a function of time after incubation of the adriamycin derivatives of the invention in buffer at pH 4.5, as described in Example 6, infra.
Figure 11:
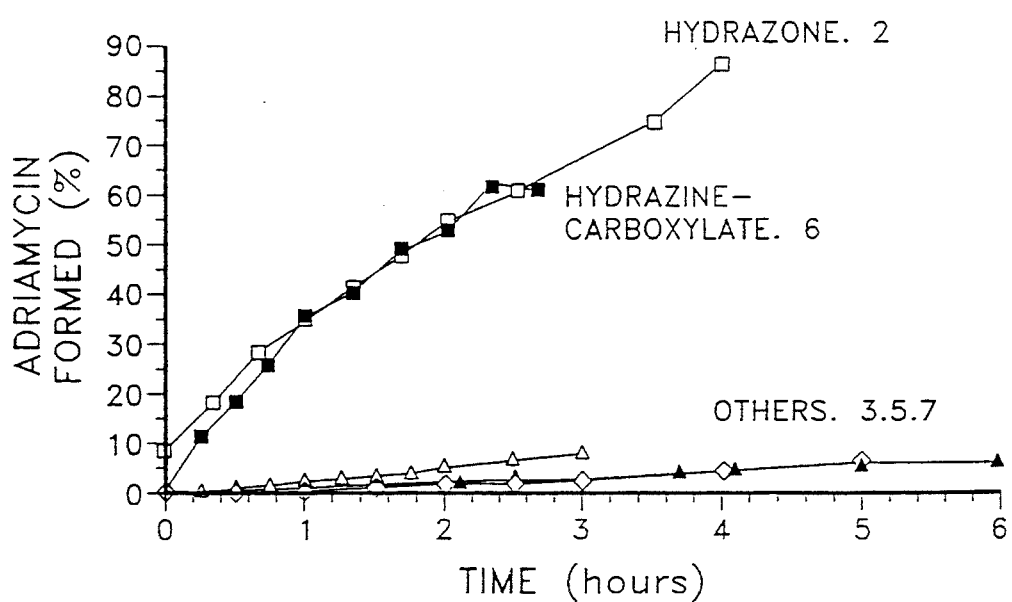
FIG. 11 is a graph of the release of adriamycin as a function of time after incubation of the adriamycin derivatives of the invention in buffer at pH 5.0, as described in Example 6, infra.
Figure 12:
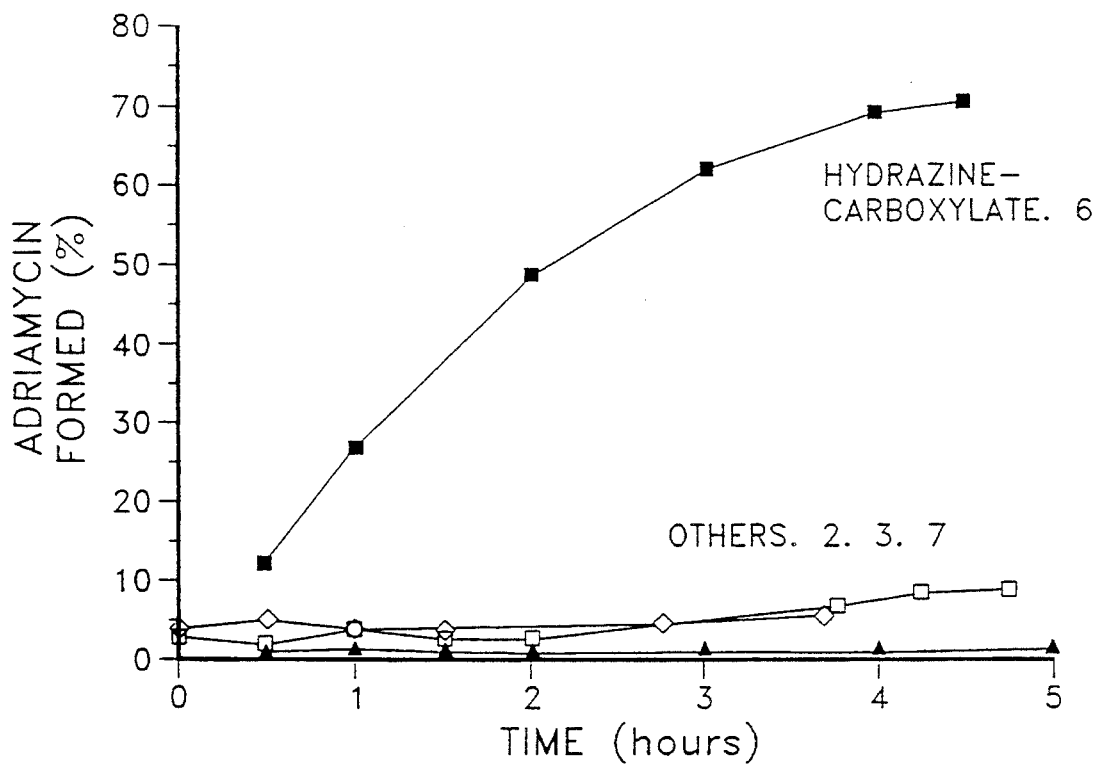
FIG. 12 is a graph of the release of adriamycin as a function of time after incubation of the adriamycin derivatives of the invention in buffer at pH 7.4, as described in Example 6, infra.

The release of ADM from the ADM derivatives of the invention prepared as described in Examples 1–5 above, at various pH's, ranging from 4.5 to 7.4, was studied using HPLC analysis. Stock solutions (1 mg/ml) of the ADM-derivatives were prepared in methanol and aliquots were diluted into aqueous buffer solution at pH 4.5, 5.0 and 7.4 to achieve final concentrations of approximately 1.6 nmol/ml. Incubations in each buffer were carried out at 37° C. for up to 24 h and the aliquots were analyzed by application to an HPLC column to determine the amount of unconjugated ADM. The released material was identified as intact ADM by its retention time on the column and by a UV profile of the eluted material. The release rates were expressed as a percentage of the maximum amount of ADM and are shown in FIGS. 10–12.

As illustrated in the figures, the ADM derivatives of the invention demonstrated wide-ranging release rates. The amount of material released from the ADM-derivatives increased as the pH was lowered from 7 to 4. The ADM-derivatives have an acid-sensitive linkage group which results in release of ADM from the antibody protein. These results are consistent with the existence of a semicarbazone, carbazone, thiosemicarbazone, carboxylatehydrazone or arylhydrazone bond joining the ADM to the bifunctional compound.

EXAMPLE 7

Preparation of Anthracycline Immunoconjugates

This example describes the preparation of anthracycline immunoconjugates according to the present invention wherein the above-described ADM derivatives (Examples 1–5) are conjugated to a monoclonal antibody.

Preparation of Immunoconjugates Having a Disulfide Bond Within the Bifunctional Compound The monoclonal antibody used was 5E9 produced from hybridoma ATCC No. HB21, available from the American Type Culture Collection "ATCC" in Rockville, Md. Monoclonal antibody 5E9 is an IgG$_1$ antibody reactive with the transferrin receptor on all dividing human cells and cross-reactive with various histological types of cancer cells. 5E9 was purified from ascitic fluid produced in BALB/c mice according to the procedure of Bruck et al., "One-Step Purification of Mouse Monoclonal Antibodies From Ascitic Fluid by DEAE-Affigel Blue Chromatography" *J. Immunol. Methods* 5b:313-319 (1982)).

Before reacting the ADM-derivative with the monoclonal antibody selected, the antibody was thiolated, i.e. to introduce reactive sulfhydryl groups onto the antibody molecule. Thiolation of the 5E9 monoclonal antibody (MAb) was performed using SPDP essentially as described by Greenfield et al., supra. Briefly, SPDP (Pierce Chemical Co., Ill.) (50 mM), dissolved in ethanol, was added to the 5E9MAb (5–10 mg/ml) in phosphate buffered saline (PBS), pH 7.2, to give a final concentration of between 5–10 mM. The reaction mixture was incubated for 30 min at 30° C. Unreacted SPDP was separated from SPDP-derivatized antibody by gel filtration chromatography using a PD-10 column (Pharmacia). The reactive pyridinyldithio moieties were removed by reduction with excess DTT. The reduced antibodies were passed through a PD-10 column and the free thiol-containing antibodies were used for condensation with the ADM derivatives.

Reactive thiol groups were also introduced onto the antibody protein using 2-IT. The antibody (5–10 mg/ml in 50 mM TEA, 50 mM NaCl, 1 mM EDTA at pH 8.0) was mixed with 2-IT (Pierce Chemical Co., Ill.) at a final concentration of 5–10 mM. The reaction was allowed to proceed for 90 min at 4° C. and thiolated antibodies were separated on a PD-10 column equilibrated with 2M NaCl/PBS.

The number of reactive thiol groups incorporated onto the antibody was determined using DTNB (5,5'-dithiobis-(2-nitrobenzoic acid) ($E_{412}=14150$) according to the procedure described by Ellman, *Arch. Biochem. Biophys.* 82:70-77 (1959)).

Each ADM-derivative was dissolved in DMF and added to the reduced SPDP-thiolated MAb 5E9 in PBS. The amount of ADM-derivative was equivalent to the number of thiol groups on the antibody. The conjugation reaction was allowed to incubate overnight at 4° C. After this period the antibody solution was dialyzed against PBS to remove unconjugated adriamycin derivative. The antibody solution was then treated with SM-2 BioBeads (Bio-Rad Laboratories, Richmond, Calif.) overnight. The amount of conjugated anthracycline bound to the MAb was determined by absorbance at 495 nm ($E_{495}=8030$). The amount of antibody protein was determined by absorbance at 280 nm (1 mg/ml = 1.40 O.D. units). To correct for the overlap of ADM absorbance at 280 nm, the following formula was used:

$$\text{Antibody (mg/ml)} = \frac{A_{280} - (0.72 \times A_{495})}{1.4}$$

Immunoconjugates were analyzed for the presence of unconjugated ADM or ADM derivatives using HPLC analysis. HPLC was done using a Phenomenex column packed with 5 micron IB-SIL C18 beads. Unconjugated drug, ADM-derivatives (i.e. ADM conjugated to each of the bifunctional compounds of the invention prepared as described in Examples 1–5 above) (0.1 $\mu$moles). or immunoconjugates containing 0.5–5 $\mu$moles drug equivalents were applied to the column and eluted with methanol and 10 mM ammonium phosphate, pH 4.5 (70:30) at 1.5 ml/min. The immunoconjugates produced contained no significant amount (less than 1%) of unconjugated drug as determined by HPLC analysis.

EXAMPLE 8

Characterization of the Immunoconjugates

The immunoconjugates produced as described above in Example 7 were comprised of ADM molecules conjugated at the 13-keto position to a bifunctional compound that formed a link between the ADM and MAb 5E9. Furthermore, the addition of the MAb with free thiol groups to the ADM derivative which contained a reactive pyridinyldithio moiety, led to the formation of a disulfide bond in the bifunctional compound joining ADM to the MAb. Immunoconjugates formed according to this embodiment include, but are not limited to, 5E9-ADM-semicarbazone-[3.42]; 5E9-ADM-carbazone-[4.37]; 5E9-ADM-thiosemicarbazone-[2.51]; 5E9-ADM-carboxylatehydrazone-[2.35]; and 5E9-ADM-arylhydrazone-[2.52], wherein the first part of the designation represents the monoclonal antibody used to form the conjugate, the second part represents the anthracycline linked to the antibody and the numeral in the designation represents the molar ratio of ADM/antibody in the particular conjugate.

The binding activity of the immunoconjugates of the invention was determined in a fluorescence binding assay as described by Greenfield et al., in "In Vitro Evaluation of Immunoconjugates Prepared by Linking Mitomycin C to Monoclonal Antibodies via Polyglutamic Acid Carriers" in Antibody Immunoconjugates and Radiopharmaceuticals, Vol. 2, p. 201 (1989). Briefly, the immunoconjugates were serially diluted into 100 $\mu$l assay media (RPMI 1640 supplemented with 10% fetal calf serum and penicillin/streptomycin, Gibco, Grand Island, N.Y.). CEM tumor cells (ATCC No. CCL 119) ($1 \times 10^6$ cells) grown in the same medium were harvested and washed by centrifugation and then suspended ($1 \times 10^6$) in the medium containing the diluted immunoconjugates. After one hour of incubation at 4° C., cells were washed and suspended in 100 $\mu$l medium containing 1:40 diluted goat anti-mouse IgG-FITC (Cappel, Durham, N.C.) for additional one hour at 4° C. Cells were washed and analyzed using a Coulter Epics V fluorescence cell analyzer. For each experiment, similarly diluted MAb was used as a non-conjugated positive binding control. The percentage of protein yield (obtained separately), molar ratios (moles of ADM/MAb) and binding expressed as the percentage of original binding are shown in Table 1.

TABLE 1

| 5E9 Immuno-conjugate | Protein Yield (%) | Molar Ratios | (% Orig. Binding) |
| --- | --- | --- | --- |
| Semicarbazone | 83 | 3.42 | 97 |
| Carbazone | 74 | 4.37 | 92 |
| Thiosemicarbazone | 61 | 2.51 | 72 |
| Carboxylate-Hydrazone | 78 | 2.35 | 97 |
| Arylhydrazone | 86 | 2.52 | 91 |

As shown in Table 1, the 5E9 immunoconjugates retained over 90% (except for thiosemicarbazone) of the original binding activity of the unconjugated 5E9. This demonstrates that the conjugation of the ADM derivatives to the 5E9MAb resulted in the loss of relatively small degrees of antibody binding activity. The protein yields indicate that high amounts of protein were retained throughout the conjugation procedure.

Release of ADM From The Carbazone Immunoconjugate

Figure 13:
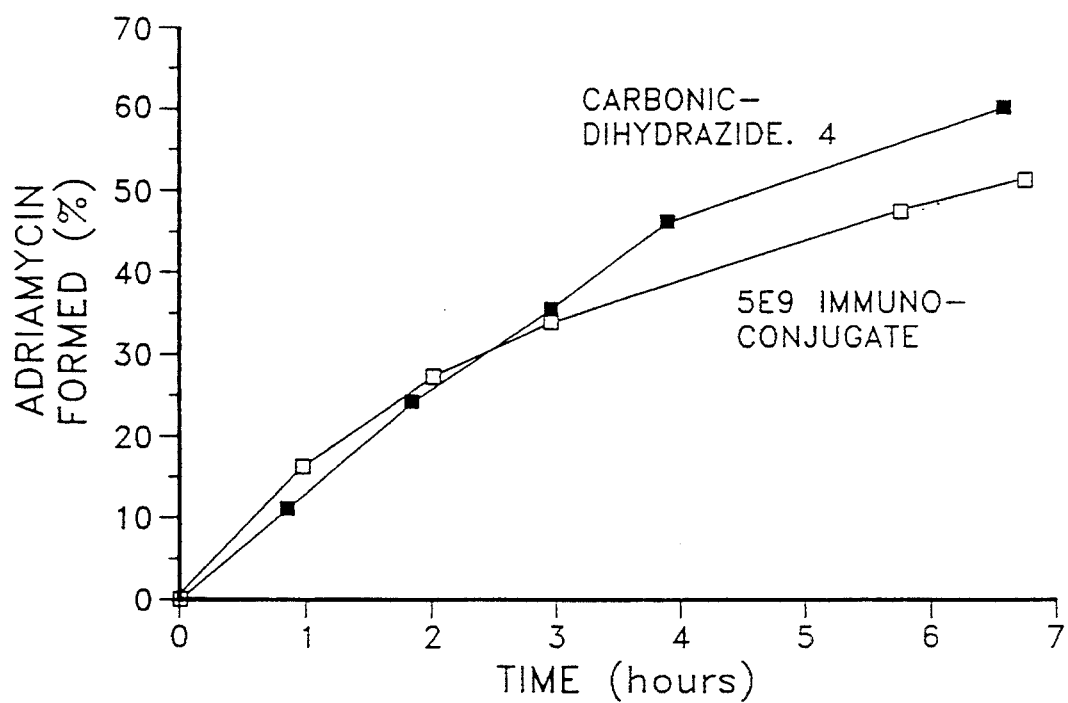
FIG. 13 is a graph of the release of adriamycin from the carbazone derivative of adriamycin and from a 5E9 immunoconjugate of this derivative, as a function of time after incubation in buffer at pH 4.5, as described in Example 7, infra.

The release rates of ADM from the carbazone immunoconjugate of the invention at pH 4.5, 5.0 and 7.4 were also studied by HPLC analysis as described above in Example 6 for the ADM-derivatives of the invention. As shown in FIG. 13, the release rate of ADM from the immunoconjugate is essentially the same as that shown for the carbazone derivative of ADM in Example 6. The amount of material released from the ADM-immunoconjugate increased as the pH was lowered from 7 to 4. This ADM-immunoconjugate has an acid-sensitive linkage group which results in release of ADM from the antibody protein. These results are consistent with the existence of a hydrazone bond joining the ADM to the bifunctional compound.

The experimental data described herein demonstrate that an ADM moiety is released from the immunoconjugates of this invention under "physiologic" conditions, i.e. acidic conditions typical of the lysosomal environment.

Cytotoxic Activity of the Immunoconjugates

The cytotoxicity of the immunoconjugates of the invention was determined by in vitro testing using the Colony Formation Assay in soft agar using Daudi(Burkitt's lymphoma) cells (phenotype: 5E9+, ATCC No. HB21) as described by Greenfield et al., European Patent Application No. 328,147, supra. The Daudi cells were grown in complete medium (RPMI 1640 medium plus 10% fetal calf serum (FCS)). $1 \times 10^5$ cells in 1 ml of medium were exposed for 1.5 hours to serially diluted 5E9-ADM immunoconjugates or unconjugated ADM. Triplicate determinations were done for each dilution. Controls consisted of similarly treated cells not exposed to drugs. The cells were then washed and suspended in RPMI 1640 medium containing 15% FBS and 0.3% agarose (Marine Colloid, Rockland, Me.). One ml of the cell suspension ($1 \times 10^3$) cells was then overlayed onto a 0.4% agarose layer in 6 well microtiter plates (Costar, Cambridge, Mass.). Samples were incubated for 7–10 days at 37° C. and the resulting colonies were stained with 0.5 ml of 1 mg/ml of p-iodonitrotetrazolium violet (Sigma Chemical Co., St. Louis, Mo.) for 48 hours. Colonies were counted using an Optimax 40–10 image analyzer and the inhibition of colony formation was determined by comparing drug-treated or immunoconjugate-treated cells to the untreated control. The results are presented in Table 2, below, as IC$_{50}$ (the concentration required to inhibit colony formation by 50% ).

TABLE 2

| 5E9 Immunoconjugate | IC$_{50}$ (M)$^a$ |
| --- | --- |
| Semicarbazone | >5.1 × 10$^{-7}$ |
| Carbazone | 4.0 × 10$^{-7}$ |
| Thiosemicarbazone | 3.0 × 10$^{-7}$ |
| Carboxylatehydrazone | 5.9 × 10$^{-7}$ |
| Arylhydrazone | >6.4 × 10$^{-7}$ |

$^a$M = molar concentration of immunoconjugate required to inhibit colony formation by 50% measured after 24 h.

As shown in Table 2, in addition to releasing ADM, all of the pH-sensitive immunoconjugates possess significant cytotoxic activity in vitro.

EXAMPLE 9

Preparation of an Anthracycline Immunoconjugate Containing a Thioether Linkage

This example describes an alternative embodiment for the preparation of an anthracycline immunoconjugate according to the present invention, wherein ADM is conjugated to a monoclonal antibody via one of the ADM-derivatives of the invention, prepared as described above in examples 1–5, and having any of the five bonds: semicarbazone, carbazone, thiosemicarbazone, carboxylatehydrazone and arylhydrazone as its site of attachment to the ADM molecule. Additionally, the immunoconjugate has a thioether linkage as part of its attachment to the antibody.

MAb 5E9 (2.5 mg in 2.5 ml of PBS) is reacted with SMPB (succinimidyl-4-(p-maleimidophenyl)butyrate 59.5 μg in 100 μl tetrahydrofuran) at 30° C. for 30 min. The pH is adjusted to 6.0 with sodium citrate buffer. The mixture is passed through a PD-10 gel filtration column (Pharmacia) to separate maleimide-containing antibody from unreacted materials. The ADM-derivatives (1 mg), prepared as described above, are then dissolved in 1 ml MeOH/H$_2$O (9:1) and 0.5 μmoles of each of the ADM-derivatives is reacted with 0.5 μmoles of tri-n-butylphosphine in 4:1 acetone:H$_2$O to prepare the reduced form of the ADM derivative. After 10 min, 0.1M sulfur in toulene is added to destroy remaining phosphine. The reduced ADM-derivatives are then mixed with the 5E9 maleimide-containing MAb. Immunoconjugates so produced are purified by passage through a PD-10 gel filtration column. In cases where removal of toluene solvent is not complete and an organic solvent layer separates floating some protein from the reaction mixture, a gentle stream of air is used to remove the solvent and the denatured protein is removed by spinning the mixture for 2 min at 16,000×g. The clear supernatant contains the immunoconjugates and is gel filtered and analyzed in PBS at pH 7.4. The ADM/antibody molar ratio is determined spectrophotometrically using OD$_{280}$ and OD$_{495}$ as described above. A typical reaction yields immunoconjugates with molar ratios between 3 and 4.

The binding and cytotoxic activity of immunoconjugates prepared as described in this example are tested as described above.

The above examples demonstrate the preparation of novel N-substituted hydrazine bifunctional compounds, novel N-substituted hydrazone derivatives of ADM made with these bifunctional compounds and novel immunoconjugates in which ADM was conjugated to an antibody via a novel acid-sensitive linkage. The bifunctional compounds were readily conjugated with a cytotoxic reagent, ADM and a cell targeting molecule, a monoclonal antibody. The conjugates retained both antibody binding activity, (i.e. target cell specificity) and cytotoxic drug activity and released free, unmodified ADM under acidic conditions typical of the cellular environment of target cells.

Thus, the novel bifunctional compounds of the invention immunoconjugates of the invention show promise for conjugating useful molecules, particularly for delivering cytotoxic drugs to a target cell population for the preferential killing of those cells in the treatment of diseases such as cancers and other tumors, non-cytocidal viral or other pathogenic infections and autoimmune disorders.

While we have hereinbefore presented a number of embodiments of this invention, it is apparent that our basic construction can be altered to provide other embodiments which utilize the bifunctional compounds, derivatives of cytotoxic reagents, conjugates and methods of this invention. Therefore, it will be appreciated that the scope of this invention is to be defined by the claims appended hereto rather than by the specific embodiments which have been presented hereinbefore by way of example.

We claim:

1. A conjugate formed by combining at least one molecule containing a free carbonyl group and at least one molecule containing a sulfhydryl group with at lease one of the following compounds:

(a) a bifunctional N-substituted hydrazine compound having the formula:

$H_2NNHCONH(CH_2)_nSSR^8$ wherein n is an integer from 1 to 10; and $R^8$ is

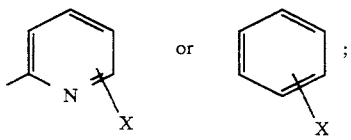

wherein X is $NO_2$ or halogen;

(b) a N-substituted hydrazine bifunctional compound having the formula:

$H_2NNHCONHNHCONH(CH_2)_nSSR^8$ wherein n is an integer from 1 to 10; and $R^8$ is

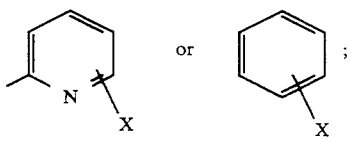

wherein X is H, $NO_2$ or halogen;

(c) a N-substituted hydrazine bifunctional compound having the formula:

$H_2NNHCSNH(CH_2)_mCH=CH(CH_2)_nSSR^8$ wherein m, n are integers from 1 to 10, which are the same or different; and $R^8$ is

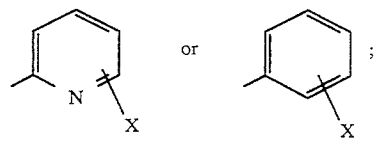

wherein X is H, $NO_2$ or halogen; or (d) a N-substituted hydrazine bifunctional compound having the formula:

$H_2NNHCOO(CH_2)_nSSR^8$ wherein n is an integer from 1 to 10; and $R^8$ is

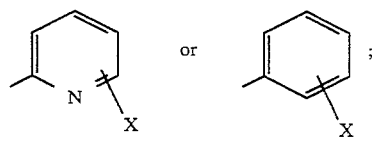

wherein X is H, $NO_2$ or halogen; or (e) a N-substituted hydrazine bifunctional compound having the formula:

$H_2NNH-Ar-CONH(CH_2)_nSSR^8$ wherein n is an integer from 1 to 10; and $R^8$ is

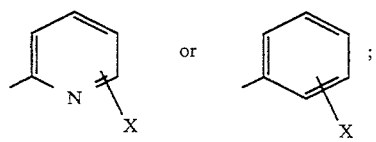

wherein X is $NO_2$ or halogen and Ar is

2. The conjugate of claim 1, wherein said molecule containing a carbonyl group is a cytotoxic reagent.

3. The conjugate of claim 2 wherein said cytotoxic reagent is an anthracycline.

4. The conjugate of claim 1, wherein said molecule containing a sulfhydryl group is a molecule reactive with a target cell population.

5. The conjugate of claim 4 wherein said molecule is a monoclonal antibody.

6. A bifunctional compound comprising the compound of 1, wherein said compound is reduced by a reducing reagent to form a free sulfhydryl group.

7. A conjugate formed by combining the compound of claim 6 with at least one molecule containing a free carbonyl group and at least one molecule having maleiimide groups attached.

8. The conjugate of claim 7 wherein said molecule containing a free carbonyl group is an anthracycline and said molecule having maleiimide groups attached is an antibody.

* * * * *